United States Patent
Kerbage et al.

(10) Patent No.: US 11,202,674 B2
(45) Date of Patent: Dec. 21, 2021

(54) LASER SYSTEM FOR SURGICAL APPLICATIONS

(71) Applicant: Convergent Dental, Inc., Needham, MA (US)

(72) Inventors: Charles Kerbage, Arlington, MA (US); Ali Badreddine, Boston, MA (US)

(73) Assignee: Convergent Dental, Inc., Needham, MA (US)

( * ) Notice: Subject to any disclaimer, the term of this patent is extended or adjusted under 35 U.S.C. 154(b) by 181 days.

(21) Appl. No.: 16/371,698

(22) Filed: Apr. 1, 2019

(65) Prior Publication Data
US 2019/0298448 A1 Oct. 3, 2019

Related U.S. Application Data

(60) Provisional application No. 62/651,987, filed on Apr. 3, 2018, provisional application No. 62/651,982, filed on Apr. 3, 2018.

(51) Int. Cl.
*A61B 18/20* (2006.01)
*A61B 90/00* (2016.01)
(Continued)

(52) U.S. Cl.
CPC ............ *A61B 18/20* (2013.01); *A61B 18/203* (2013.01); *A61B 34/20* (2016.02); *A61B 90/37* (2016.02);
(Continued)

(58) Field of Classification Search
CPC ....... A61B 34/20; A61B 18/20; A61B 18/203; A61B 90/37; A61B 2018/20359; A61B 2018/00565; A61B 2018/00577
See application file for complete search history.

(56) References Cited

U.S. PATENT DOCUMENTS 3,913,582 A 10/1975 Sharon
4,433,681 A 2/1984 Comparetto
(Continued)

FOREIGN PATENT DOCUMENTS

AU 5699690 A 5/1992
AU 639693 B2 8/1993
(Continued)

OTHER PUBLICATIONS

International Search Report and Written Opinion, dated Sep. 10, 2019 for International Application No. PCT/US2019/025125.
(Continued)

*Primary Examiner* — Gary Jackson
*Assistant Examiner* — Zahed Kabir
(74) *Attorney, Agent, or Firm* — Goodwin Procter LLP

(57) ABSTRACT

Improved systems and methods for performing laser based treatment of hard and soft tissues, e.g., bone, skin, and connective tissue, are described. The system can feature a laser adapted to produce a peak output power significantly higher than the output power produced by conventional laser-based dental treatment systems. In some instances, the system features high definition imagers for real-time, on-axis visualization and spatial measurement of the surgical region, which can include rendering 3D images. In some implementations, the system is adapted to deliver a laser beam polarized to align with the collagen fibers of bone tissue, to enhance cutting performance. In some implementations, the system is adapted to image the treatment region with polarized light, which can enable improved visualization of nerves and other anatomical structures.

19 Claims, 17 Drawing Sheets

(51) Int. Cl.
*A61B 34/20* (2016.01)
*A61B 18/00* (2006.01)

(52) U.S. Cl.
CPC .............. *A61B 2018/00565* (2013.01); *A61B 2018/00577* (2013.01); *A61B 2018/00601* (2013.01); *A61B 2018/00702* (2013.01); *A61B 2018/00726* (2013.01); *A61B 2018/00732* (2013.01); *A61B 2018/20351* (2017.05); *A61B 2018/20359* (2017.05)

(56) References Cited

U.S. PATENT DOCUMENTS

| | | |
|---|---|---|
| 4,856,513 A | 8/1989 | Muller |
| 4,932,973 A | 6/1990 | Gendler |
| 5,112,354 A | 5/1992 | Sires |
| 5,171,150 A | 12/1992 | Levy |
| 5,172,264 A | 12/1992 | Morrow |
| 5,192,279 A | 3/1993 | Samuels et al. |
| 5,236,360 A | 8/1993 | Levy |
| 5,267,856 A | 12/1993 | Wolbarsht et al. |
| 5,275,596 A | 1/1994 | Long et al. |
| 5,290,274 A | 3/1994 | Levy et al. |
| 5,304,167 A | 4/1994 | Freiberg |
| 5,313,962 A | 5/1994 | Obenchain |
| 5,342,355 A | 8/1994 | Long |
| 5,349,590 A | 9/1994 | Amirkhanian et al. |
| 5,387,211 A | 2/1995 | Saadatmanesh et al. |
| 5,388,987 A | 2/1995 | Badoz et al. |
| 5,458,594 A | 10/1995 | Mueller et al. |
| 5,498,259 A | 3/1996 | Mourant et al. |
| 5,746,738 A | 5/1998 | Cleary et al. |
| 5,860,967 A | 1/1999 | Zavislan et al. |
| 5,865,744 A | 2/1999 | Lemelson |
| 5,925,036 A | 7/1999 | Maxwell, III |
| 6,018,094 A | 1/2000 | Fox |
| 6,033,406 A | 3/2000 | Mathews |
| 6,120,498 A | 9/2000 | Jani et al. |
| 6,149,672 A | 11/2000 | Ruschke |
| 6,179,830 B1 | 1/2001 | Kokubu |
| 6,309,392 B1 | 10/2001 | Alexander et al. |
| 6,339,913 B1 | 1/2002 | Leon Fong et al. |
| 6,355,006 B1 | 3/2002 | Ryaby et al. |
| 6,390,970 B1 | 5/2002 | Muller |
| 6,395,000 B1 | 5/2002 | Mitchell et al. |
| 6,451,009 B1 | 9/2002 | Dasilva et al. |
| 6,482,199 B1 | 11/2002 | Neev |
| 6,620,185 B1 | 9/2003 | Harvie et al. |
| 6,669,685 B1 | 12/2003 | Rizoiu et al. |
| 6,669,710 B2 | 12/2003 | Moutafis et al. |
| 6,699,242 B2 | 3/2004 | Heggeness |
| 7,108,696 B2 | 9/2006 | Daniel et al. |
| 7,122,029 B2 | 10/2006 | Koop et al. |
| 7,387,614 B2 | 6/2008 | Staecker |
| 7,415,050 B2 | 8/2008 | Rizoiu et al. |
| 7,465,313 B2 | 12/2008 | DiMauro et al. |
| 7,497,868 B2 | 3/2009 | Steinberg |
| 7,507,253 B2 | 3/2009 | Nordquist |
| 7,513,906 B2 | 4/2009 | Passy et al. |
| 7,690,382 B2 | 4/2010 | Raif et al. |
| 7,708,557 B2 | 5/2010 | Rubbert |
| 7,776,048 B2 | 8/2010 | Neubauer et al. |
| 7,909,827 B2 | 3/2011 | Reiley et al. |
| 8,021,401 B2 | 9/2011 | Carl et al. |
| 8,034,091 B2 | 10/2011 | Ravussin |
| 8,172,853 B2 | 5/2012 | Michelson |
| 8,282,628 B2 | 10/2012 | Paul et al. |
| 8,343,179 B2 | 1/2013 | To et al. |
| 8,348,933 B2 | 1/2013 | Altshuler et al. |
| 8,372,061 B2 | 2/2013 | Berna et al. |
| 8,460,277 B2 | 6/2013 | Suarez et al. |
| 8,480,719 B2 | 7/2013 | Fortuna et al. |
| 8,551,750 B2 | 10/2013 | Harlow et al. |
| 8,597,352 B2 | 12/2013 | Schwartz |
| 8,663,232 B2 | 3/2014 | Michelson |
| 8,669,488 B2 | 3/2014 | Squier et al. |
| 8,702,739 B2 | 4/2014 | Batten et al. |
| 8,715,347 B2 | 5/2014 | Servell et al. |
| 8,764,739 B2 | 7/2014 | Boutoussov et al. |
| 8,790,333 B2 | 7/2014 | Shimokita |
| 8,805,547 B2 | 8/2014 | Fritsch et al. |
| 8,814,921 B2 | 8/2014 | Aljuri et al. |
| 8,821,483 B2 | 9/2014 | Boutoussov et al. |
| 8,857,442 B1 | 10/2014 | Ospina |
| 8,914,098 B2 | 12/2014 | Brennan et al. |
| 8,936,596 B2 | 1/2015 | Mittelstadt et al. |
| 8,979,853 B2 | 3/2015 | Anissian |
| 8,992,529 B2 | 3/2015 | Zeiler et al. |
| 9,017,407 B2 | 4/2015 | Donner |
| 9,055,953 B2 | 6/2015 | Lang et al. |
| 9,055,987 B2 | 6/2015 | Hulliger |
| 9,084,613 B2 | 7/2015 | Qutub |
| 9,107,977 B2 | 8/2015 | Kanaoka et al. |
| 9,119,649 B2 | 9/2015 | van der Weide et al. |
| 9,131,990 B2 | 9/2015 | Draenert |
| 9,162,015 B2 | 10/2015 | Johnson et al. |
| 9,168,140 B2 | 10/2015 | Shi et al. |
| 9,186,380 B2 | 11/2015 | Shi et al. |
| 9,192,418 B2 | 11/2015 | Kanaoka et al. |
| 9,192,438 B2 | 11/2015 | Thiel et al. |
| 9,192,459 B2 | 11/2015 | Bonutti |
| 9,237,914 B2 | 1/2016 | Nardini et al. |
| 9,339,279 B2 | 5/2016 | Dubois et al. |
| 9,345,460 B2 | 5/2016 | Houser et al. |
| 9,387,041 B2 | 7/2016 | Dahotre et al. |
| 9,402,726 B2 | 8/2016 | Linderman et al. |
| 9,463,010 B2 | 10/2016 | Gittings et al. |
| 9,474,910 B1 | 10/2016 | Servell et al. |
| 9,554,909 B2 | 1/2017 | Donner et al. |
| 9,572,632 B2 | 2/2017 | Lukac et al. |
| 9,610,110 B2 | 4/2017 | Truckai et al. |
| 9,615,841 B2 | 4/2017 | Eder |
| 9,649,505 B2 | 5/2017 | Oron et al. |
| 9,687,669 B2 | 6/2017 | Stephan |
| 9,724,107 B2 | 8/2017 | Pellegrino et al. |
| 9,744,043 B2 | 8/2017 | Chen et al. |
| 2002/0193780 A1 | 12/2002 | Karray et al. |
| 2003/0114902 A1 | 6/2003 | Prescott |
| 2004/0010251 A1 | 1/2004 | Pitaru et al. |
| 2004/0188011 A1 | 9/2004 | Jones |
| 2005/0049703 A1 | 3/2005 | Lee |
| 2005/0096655 A1 | 5/2005 | Trinchese |
| 2005/0222681 A1 | 10/2005 | Richley et al. |
| 2005/0272610 A1 | 12/2005 | Ivanov et al. |
| 2006/0089609 A1 | 4/2006 | Bleich et al. |
| 2006/0122582 A1 | 6/2006 | Caldera et al. |
| 2006/0142745 A1 | 6/2006 | Boutoussov |
| 2006/0142870 A1 | 6/2006 | Robinson et al. |
| 2006/0146284 A1* | 7/2006 | Collins ............... A61B 3/1208 351/215 |
| 2006/0210644 A1 | 9/2006 | Levin |
| 2007/0005120 A1 | 1/2007 | Villacampa et al. |
| 2007/0093797 A1 | 4/2007 | Chan et al. |
| 2007/0161852 A1 | 7/2007 | Raimondi |
| 2007/0162093 A1 | 7/2007 | Porter et al. |
| 2007/0239153 A1 | 10/2007 | Hodorek et al. |
| 2007/0270864 A1 | 11/2007 | Gurtowski |
| 2008/0077251 A1 | 3/2008 | Chen et al. |
| 2008/0132899 A1 | 6/2008 | Shadduck et al. |
| 2009/0105792 A1 | 4/2009 | Kucklick |
| 2010/0100084 A1 | 4/2010 | Girard et al. |
| 2010/0239635 A1 | 9/2010 | McClain et al. |
| 2011/0189628 A1* | 8/2011 | Monty ................. H01S 3/2232 433/29 |
| 2011/0201075 A1 | 8/2011 | Koller et al. |
| 2011/0213350 A1 | 9/2011 | Ezenwa et al. |
| 2011/0270241 A1 | 11/2011 | Boutoussov |
| 2012/0053577 A1 | 3/2012 | Lee et al. |
| 2012/0165952 A1 | 6/2012 | Stinnette |
| 2012/0220992 A1 | 8/2012 | Bruno et al. |
| 2012/0221007 A1 | 8/2012 | Batten et al. |
| 2012/0232557 A1 | 9/2012 | Nakagawa et al. |
| 2012/0265186 A1 | 10/2012 | Burger et al. |
| 2013/0011815 A1 | 1/2013 | Henig et al. |

(56) References Cited

U.S. PATENT DOCUMENTS

| | | | |
|---|---|---|---|
| 2013/0059264 A1* | 3/2013 | Monty | A61C 1/0046 433/29 |
| 2013/0095071 A1 | 4/2013 | Bance et al. | |
| 2013/0178855 A1 | 7/2013 | Loquet et al. | |
| 2013/0253519 A1 | 9/2013 | Mitchell et al. | |
| 2014/0170588 A1 | 6/2014 | Miller et al. | |
| 2014/0195030 A1 | 7/2014 | Farwell | |
| 2014/0371717 A1 | 12/2014 | McClain et al. | |
| 2014/0371827 A1 | 12/2014 | Mohamed et al. | |
| 2015/0038790 A1 | 2/2015 | Rontal et al. | |
| 2015/0150650 A1 | 6/2015 | Netchitailo et al. | |
| 2015/0151380 A1 | 6/2015 | Hosseini | |
| 2015/0157406 A1 | 6/2015 | Hipsley | |
| 2015/0165243 A1 | 6/2015 | Slayton et al. | |
| 2015/0196369 A1 | 7/2015 | Glossop | |
| 2015/0238261 A1 | 8/2015 | Monty et al. | |
| 2015/0327930 A1 | 11/2015 | Bruno et al. | |
| 2015/0343234 A1 | 12/2015 | Ovokaitys et al. | |
| 2016/0008007 A1 | 1/2016 | Taha | |
| 2016/0081758 A1 | 3/2016 | Bonutti | |
| 2016/0135890 A1 | 5/2016 | Cattin et al. | |
| 2016/0135906 A1 | 5/2016 | Cattin et al. | |
| 2016/0367267 A1 | 12/2016 | Marino et al. | |
| 2017/0014640 A1 | 1/2017 | Kariguddaiah | |
| 2017/0112571 A1 | 4/2017 | Thiel et al. | |
| 2017/0120345 A1 | 5/2017 | Patten et al. | |
| 2017/0181755 A1 | 6/2017 | Librot | |
| 2017/0258962 A1 | 9/2017 | Tabbaa et al. | |
| 2018/0049642 A1* | 2/2018 | Mak | A61B 90/37 |

FOREIGN PATENT DOCUMENTS

| | | | | |
|---|---|---|---|---|
| BG | 111401 | A | | 9/2014 |
| BR | 102014007397 | A2 | | 3/2016 |
| CA | 2045064 | A1 | | 4/1992 |
| CA | 2019334 | C | | 7/2001 |
| CA | 2958962 | A1 | | 4/2010 |
| CA | 2745016 | A1 | | 6/2010 |
| CA | 2812775 | A1 | | 2/2011 |
| CA | 2728950 | A1 | | 3/2012 |
| CA | 2889478 | A1 | | 5/2014 |
| CA | 2894750 | A1 | | 8/2014 |
| CA | 2931616 | A1 | | 6/2015 |
| CA | 2740734 | C | | 4/2017 |
| CA | 2946649 | C | | 3/2018 |
| CH | 698706 | B1 | | 10/2009 |
| CN | 1100920 | C | | 2/2003 |
| CN | 101190147 | A | | 6/2008 |
| CN | 100484487 | C | | 5/2009 |
| CN | 101259028 | B | | 4/2011 |
| CN | 102078642 | B | | 10/2013 |
| CN | 102599961 | B | | 10/2013 |
| CN | 203263531 | U | | 11/2013 |
| CN | 104799980 | A | | 7/2015 |
| CN | 103202724 | B | | 9/2015 |
| CN | 102805677 | B | | 11/2015 |
| CN | 106108976 | A | | 11/2016 |
| CN | 205697913 | U | | 11/2016 |
| CN | 106510900 | A | | 3/2017 |
| CN | 106078848 | B | | 3/2018 |
| CN | 106512084 | B | | 4/2019 |
| CN | 109803600 | A * | 5/2019 | A61B 34/32 |
| DE | 2455334 | A1 | | 5/1976 |
| DE | 3816456 | A1 | | 11/1989 |
| DE | 4138468 | A1 | | 6/1993 |
| DE | 9411754 | U1 | | 11/1994 |
| DE | 29515210 | U1 | | 1/1996 |
| DE | 19507939 | A1 | | 8/1996 |
| DE | 10140812 | A1 | | 11/2002 |
| DE | 102007007915 | A1 | | 8/2008 |
| DE | 102006031356 | B4 | | 2/2012 |
| EP | 0626229 | A1 | | 11/1994 |
| EP | 0957790 | B1 | | 12/2003 |
| EP | 1613231 | A2 | | 1/2006 |
| EP | 1574170 | B1 | | 4/2007 |
| EP | 2107891 | A1 | | 10/2009 |
| EP | 1886640 | B1 | | 11/2009 |
| EP | 2000108 | B1 | | 1/2011 |
| EP | 2618768 | A1 | | 7/2013 |
| EP | 2763618 | A1 | | 8/2014 |
| EP | 2818131 | A1 | | 12/2014 |
| EP | 3127501 | A1 | | 2/2017 |
| EP | 2999418 | B1 | | 8/2017 |
| EP | 3235453 | A1 | | 10/2017 |
| FR | 2917284 | A1 | | 12/2008 |
| JP | H0759792 | B2 | | 6/1995 |
| JP | H09283863 | A | | 10/1997 |
| JP | 2001161709 | A | | 6/2001 |
| JP | 2004290333 | A | | 10/2004 |
| JP | 2007296250 | A | | 11/2007 |
| KR | 200177456 | Y1 | | 4/2000 |
| KR | 200330548 | Y1 | | 10/2003 |
| KR | 20050014946 | A | | 2/2005 |
| KR | 100818550 | B1 * | 4/2008 | |
| KR | 20090117544 | A | | 11/2009 |
| KR | 101494758 | B1 | | 2/2015 |
| KR | 101742740 | B1 | | 6/2017 |
| RU | 1819633 | C | | 6/1993 |
| RU | 2155620 | C2 | | 9/2000 |
| RU | 2209595 | C2 | | 8/2003 |
| RU | 2235522 | C1 | | 9/2004 |
| RU | 2262322 | C2 | | 10/2005 |
| RU | 2350365 | C1 | | 3/2009 |
| RU | 2386420 | C1 | | 4/2010 |
| RU | 2387401 | C2 | | 4/2010 |
| RU | 2547610 | C1 | | 4/2015 |
| RU | 2551941 | C1 | | 6/2015 |
| RU | 2581711 | C1 | | 4/2016 |
| RU | 2014138509 | A | | 4/2016 |
| RU | 2599370 | C1 | | 10/2016 |
| SU | 1113928 | A1 | | 5/1985 |
| SU | 1196010 | A1 | | 12/1985 |
| TW | M469045 | U | | 1/2014 |
| UA | 82020 | C2 | | 2/2008 |
| UA | 95706 | C2 | | 8/2011 |
| WO | WO-1985002532 | | | 6/1985 |
| WO | WO-1991011966 | | | 8/1991 |
| WO | WO-1993021843 | | | 11/1993 |
| WO | WO-1993025156 | | | 12/1993 |
| WO | WO-1997000047 | | | 1/1997 |
| WO | WO-1997007928 | | | 3/1997 |
| WO | WO-1997010768 | | | 3/1997 |
| WO | WO-2000009043 | A1 | | 2/2000 |
| WO | WO-2000035511 | A1 | | 6/2000 |
| WO | WO-2001000271 | A1 | | 1/2001 |
| WO | WO-2001072323 | A3 | | 6/2002 |
| WO | WO-200276552 | A1 | | 10/2002 |
| WO | WO-2002085262 | A1 | | 10/2002 |
| WO | WO-2003063696 | A1 | | 8/2003 |
| WO | WO-2003075801 | A1 | | 9/2003 |
| WO | WO-2005058207 | A1 | | 6/2005 |
| WO | WO-2005096783 | A3 | | 12/2005 |
| WO | WO-2005105208 | A3 | | 2/2006 |
| WO | WO-2006019756 | A3 | | 4/2006 |
| WO | WO-2006074486 | A3 | | 9/2006 |
| WO | WO-2005070034 | A3 | | 1/2007 |
| WO | WO-2007038975 | A1 | | 4/2007 |
| WO | WO-2007047435 | A1 | | 4/2007 |
| WO | WO-2007047892 | A1 | | 4/2007 |
| WO | WO-2007091155 | A1 | | 8/2007 |
| WO | WO-200699594 | A3 | | 11/2007 |
| WO | WO-2004107955 | A3 | | 1/2008 |
| WO | WO-2008116203 | | | 9/2008 |
| WO | WO-200903014 | A3 | | 3/2009 |
| WO | WO-200990643 | A3 | | 3/2010 |
| WO | WO-2010059734 | A1 | | 5/2010 |
| WO | WO-2010104053 | A1 | | 9/2010 |
| WO | WO-2010148125 | A1 | | 12/2010 |
| WO | WO-2011066522 | A3 | | 7/2011 |
| WO | WO-2011107117 | A1 | | 9/2011 |
| WO | WO-2012097506 | A1 | | 7/2012 |
| WO | WO-2012100033 | A1 | | 7/2012 |
| WO | WO-2012100048 | A1 | | 7/2012 |

(56) References Cited

FOREIGN PATENT DOCUMENTS

| WO | WO-2012110528 A3 | 11/2012 |
|---|---|---|
| WO | WO-2014045312 A1 | 3/2014 |
| WO | WO-2013114376 A8 | 4/2015 |
| WO | WO-201577439 A1 | 5/2015 |
| WO | WO-2016119040 A1 | 8/2016 |
| WO | WO-2016142270 A1 | 9/2016 |
| WO | WO-2016154356 A1 | 9/2016 |
| WO | WO-2016028680 A9 | 11/2016 |
| WO | WO-2017042168 A1 | 3/2017 |
| WO | WO-2017055362 A1 | 4/2017 |
| WO | WO-2017070637 A1 | 4/2017 |
| WO | WO-2017083992 A1 | 5/2017 |
| WO | WO-2017147140 A1 | 8/2017 |
| WO | WO-2017179010 A1 | 10/2017 |
| WO | WO-2017173333 A3 | 11/2017 |

OTHER PUBLICATIONS

Ertl, et al., "Hard Tissue Ablation With Pulsed CO2 Lasers", SPIE vol. 1800 pp. 176-181 (.

Gerold K.H. Eyrich, "Laser-osteotomy induced changes in bone", Medical Laser Application 20 (2005) 25-36.

M. Frentzen, et al., "Osteotomy with 80µs CO2 laser pulses—histological results", Lasers Med Sci (2003)18:119-124.

Werner, et al., "CO2 laser free-form processing of hard tissue", Therapeutic Laser Applications and Laser-Tissue Interactions III, Feb. 24, 2010 vol. 6632 663202-1-663202-6.

Ivanenko, et al., Ablation of hard bone tissue with puled CO2 Lasers, Medical Laser Application 20 (2005) 13-23.

G. D. Rajitha Gunaratne, Riaz Khan, Daniel Fick, Brett Robertson, Narendra Dahotre & Charlie Ironside (2016): A review of the physiological and histological effects of laser osteotomy, Journal of Medical Engineering & Technology, DOI: 10.1080/03091902.2016.1199743 (published online Jun. 27, 2016).

Ivanenko, et al., "Hard tissue ablation with sub-µs CO2 laser pulses with the use of air-water spray", Optical Biopsy and Tissue Optics, Proceedings of SPIE vol. 4161 (2000).

Ivanenko, et al., "In Vivo animal trials with a scanning CO2 laser Osteotome," Lasers in Surgery and Medicine 37:144-148 (2005).

Ivanenko, et al., "System development and clinical studies with a scanning CO2 laser osteotome," Optical Interactions with Tissue and Cells XVII, Proc. of SPIE vol. 6084, 60840H, (2006) 1605-7422.

Kahrs, et al., "Planning and simulation of microsugrical laser bone ablation," Int J CARS (2010) 5:155-162 (DOI 10.1007/s11548-009-0303-4).

Kuttenberger, et al., "Bone healing of the sheep tibia shaft after carbon dioxide laser osteotomy; histological results," Lasers Med Sci (2010) 25:239-249 (DOI 10.1007/s10103-009-0714-z).

Nair, et al., "Observations on pulpal response to carbon dioxide laser drilling of dentine in healthy human third molars," Lasers in Medical Science (2005) 19: 240-247 (DOI 10.1007/s10103-004-0317-7).

Werner, et al., "CO2 laser "milling" of hard tissue" Optical Interactions with Tissue and Cells XVIII, Proc. of SPIE vol. 6435, 64350E, (2007) 1605-7422.

Zhang, et al., "Optimization of Line Cut Strategy for Bone tissue ablation using Short-pulsed CO2 laser based on thermal relaxation."

Kuttenberger, et al., "Computer-Guided CO2-laser osteotomy of the SheepTibia: Technical prerequisites and first resultes," Photomedicine and Laser Surgery, vol. 26, No. 2, 2008, pp. 129-136 (DOI: 10.1089/pho.2007.2139).

Jud et al. "Trabecular bone anisotropy imaging with a compact laser-undulator synchrotron x-ray source",Sci Rep. Nov. 3, 2017;7(1):14477.

da Silva, et al., "Repair of Bone Defects Treated with Autogenous Bone Graft and Low-Power Laser," Journal of Craniofacial Surgery: Mar. 2006—vol. 17—Issue 2—p. 297-301.

Jahn et al., The elaboration of excimer laser dosimetry for bone and meniscus cutting and drilling using optical fibers; Proceedings of lasers in orthopedic, dental, and veterinary medicine : Jan. 23-24, 1991, Los Angeles, Calif. Bellingham, Wash., 1991 (Proceedings /SPIE 1424), S. 23-32.

Khadra, M. et al., "Enhancement of bone formation in rat calvarial bone defects using low-level laser therapy", Oral Surg Oral Med Oral Pathol Oral Radiol Endod. Jun. 2004;97(6):693-700.

Ran An et al. "Ultrafast laser ablation and machining large-size structures on porcine bone", J. of Biomedical Optics, 18(7) Jul. 2013.

Shakouri, et al. Effect of low-level laser therapy on the fracture healing process. Lasers Med Sci. Jan. 2010;25(1):73-7. doi: 10.1007/s10103-009-0670-7. Epub Apr. 28, 2009.

Lewandrowski, et al., Use of the Er:YAG laser for improved plating in maxillofacial surgery: Comparison of bone healing in laser and drill osteotomies, Lasers Surg. Med. (1996), 19: 40-45. <https://doi.org/10.1002/(SICI) 1096-9101 (1996)19:1 <40::AID-LSM6>.

Ueda et al. "Pulse irradiation of low-power laser stimulates bone nodule formation", Journal of Oral Science, 2001 vol. 43 Issue 1 pp. 55-60.

Zhen Li et al. "Photothermal ablation of bone metastasis of breast cancer using PEGylated multi-walled carbon nanotubes", Scientific Reports 5, Article 11709 (2015).

Ahrar, et al. Magnetic resonance imaging-guided laser ablation of bone tumors; Tech Vasc Interv Radiol. Sep. 2011;14(3):177-82.

Armstrong, et al., Ultrashort pulse laser ossicular ablation and stapedotomy in cadaveric bone, Lasers Surg. Med. (2002), 30: 216-220. doi:10.1002/lsm.10034 <https://doi.org/10.1002/lsm.10034>.

Guzzardella, et al., "Laser Stimulation on Bone Defect Healing: An In Vitro Study," Lasers Med Sci (2002) 17: 216-220.

Ivanenko et al., "Ablation of hard bone tissue with pulsed CO2 lasers", Medical Laser Application, vol. 20, Issue 1, May 31, 2005, pp. May 13-23, 2005.

Nelson et al., Ablation of bone and methacrylate by a prototype mid-infrared erbium:YAG laser; YAG laser. Lasers Surg. Med., 8: 494-500. (First published 1988) doi:10.1002/lsm.1900080508 <https://doi.org/10.1002/lsm.1900080508>.

Rupprecht, et al., Er:YAG laser osteotomy directed by sensor controlled systems, Elsevier, vol. 31, Issue 6, Dec. 2003, pp. 337-342.

Gangi et al. "Interventional Radiology With Laser in Bone and Joint" Radiologic Clinics of North America vol. 36, Issue 3, May 1, 1998, pp. 547-557.

Hafez et al. "Ablation of Bone, Cartilage, and Facet Joint Capsule Using Ho:YAG Laser" Journal of Clinical Laser Medicine of Surgery, vol. 20, No. 5, Jul. 8, 2004.

Walsh et al., Er:YAG laser ablation of tissue: Measurement of ablation rates Lasers Surg. Med., 9: 327-337 (1989). doi:10.1002/lsm.1900090404 <https://doi.org/10.1002/lsm.1900090404>.

Biyikli, et. al., Energy requirements for osteotomy of femora and tibiae with a moving CW CO2 laser, Lasers Surg. Med.(1987), 7: 512-519. doi:10.1002/lsm.1900070614 <https://doi.org/10.1002/lsm.1900070614>.

Morphological Changes of Bovine Mandibular Bone Irradiated by Er,Cr:YSGG Laser: An in Vitro Study (last accessed Oct. 8, 2019).

Jowett et al. "Bone Ablation without Thermal or Acoustic Mechanical Injury via a Novel Picosecond Infrared Laser (PIRL)", Otolargygology—Head and Neck Surgery Foundation, vol. 150, Issue 3, pp. 385-393, Dec. 27, 2013.

Dressel, et al., Studies in fiber guided excimer laser surgery for cutting and drilling bone and meniscus, Lasers Surg. Med. (1991), 11: 569-579. doi:10.1002/lsm.1900110612 <https://doi.org/10.1002/lsm.1900110612>.

Leucht, et al., Accelerated Bone Repair After Plasma Laser Corticotomies, Ann Surg. Jul. 2007; 246(1): 140-150. doi: 10.1097/01.sla.0000258559.07435.b3 <//dx.doi.org/10.1097%2F01.sla.0000258559.07435.b3>.

Lopes et al., "The effect of the association of near infrared laser therapy, bone morphogenetic proteins, and guided bone regeneration on tibial fractures treated with internal rigid fixation: A Raman

(56) References Cited

OTHER PUBLICATIONS spectroscopic study", Journal of Biomedical Materials Research, vol. 94A, Issue 4, Sep. 15, 2010.
Laibangyang et al. "Modeling Ultrafast Laser Ablation on the Glenoid Bone for the Fitting of a Prosthetic Screw" Group 7 BEE 4530 (last accessed Oct. 8, 2019).
R. Hibst, Mechanical effects of erbium:YAG laser bone ablation, Lasers Surg. Med. (1992), 12: 125-130. doi:10.1002/lsm.1900120203 <https://doi.org/10.1002/lsm.1900120203>.
Burgner, et. al., Ex vivo accuracy evaluation for robot assisted laser bone ablation, Int. J. Med. Robotics Comput. Assist. Surg. (2010), 6: 489-500. doi:10.1002/rcs.366 <https://doi.org/10.1002/rcs.366>.
Stein, et al., Acute and chronic effects of bone ablation with a pulsed holmium laser, Lasers Surg. Med. (1990), 10: 384-388. doi:10.1002/lsm.1900100412 <https://doi.org/10.1002/lsm.1900100412>.
Kaul et al. "Osteoid Osteoma with a Multicentric Nidus: Interstitial Laser Ablation under MRI Guidance", Case Reports in Orthopedics, vol. 2016, Article ID 254825, 5pgs, May 2013.
Fried, et. al., Comparison of Er:YAG and 9.6-µm TE CO2 lasers for ablation of skull tissue, Lasers Surg. Med. (2001), 28: 335-343. doi:10.1002/lsm.1059 <https://doi.org/10.1002/lsm.1059>.
Laser-cutting of bones replaces sawing, R&D Funding Life Sciences, Nominated for the CTI Swiss Medtech Award 2015.
Weber, et al. "Photomedicine and Laser Surgery",Photomedicine and Laser Surgery vol. 24 Issue 1: Feb. 27, 2006.
Motamedi et al. "Percutaneous Image-Guided Musculoskeletal Tumor Treatments" American Journal of Roentgenology, vol. 207: 517-525, Sep. 2016.
Sasaki et al., Ultrastructural analysis of bone tissue irradiated by Er:YAG Laser, Laser. Lasers Surg. Med. (2002), 31: 322-332. doi:10.1002/lsm.10110 <https://doi.org/10.1002/lsm.10110>.
Hestericova, M. et al., "Scientific MIRACLE: lasers and augmented reality for better bone surgeries", Sci Five, Universal of Basil, May 2017.
Pourzarandian, et al., Histological and TEM Examination of Early Stages of Bone Healing after Er:YAG Laser Irradiation, Photomedicine and Laser Surgery 2004 22:4, 342-350.
Youn et al. "A comparison of mass removal, thermal injury, and crater morphology of cortical bone ablation using wavelengths 2.79, 2.9, 6.1, and 6.45 µm", Lasers in Surgery and Medicine, vol. 39, Issue 4, Apr. 24, 2007, pp. 332-340.
Kim, et. al., An Er:YAG laser bone cutting manipulator for precise rotational acetabular osteotomy, Conf Proc IEEE Eng Med Biol Soc. 2004;4:2750-3.
Hethcock, B., "Will bone-cutting lasers replace surgical saws and drills?", Dallas Business Journal, Apr. 26, 2013.
Witt et al. "Interstitial laser photocoagulation for the treatment of osteoid osteoma", The Journal of Bone and Joint Surgery. British volume vol. 82-B, No. 8 (published online Nov. 1, 2000).
Neev et al. "Ultrashort pulse lasers for hard tissue ablation" IEEE Journal of Selected Topics in Quantum Electronics, vol. 2 Issue: 4, Dec. 1996.
de Mello, et al., Comparative histological analysis of bone healing of standardized bone defects performed with the Er:YAG laser and steel burs, Lasers Med Sci (2008) 23: 253. https://doi.org/10.1007/s10103-007-0475-5.
Payne, JT, et al., "Cortical bone healing following laser osteotomy using 6.1 microm wavelength", Lasers Surg Med. 2001;29(1):38-43.
Esteves, JC, et al,, Effects on Bone Repair of Osteotomy With Drills or With Erbium, Chromium: Yttrium-Scandium-Gallium-Garnet Laser: Histomorphometric and Immunohistochemical Study, J Periodontol. Apr. 2016;87(4):452-60. doi: 10.1902/jop.2015.150406.
Sella et al. "Effect of low-level laser therapy on bone repair: a randomized controlled experimental study." Lasers Med Sci. Apr. 2015;30(3):1061-8.
Burgner-Kahrs, et. al., Robot assisted laser bone processing: Marking and cutting experiments, Phys Med Biol. Jun. 21, 2008;53(12):3381-90. doi: 10.1088/0031-9155/53/12/021. Epub Jun. 3, 2008.

Pinheiro, A. et al. "Effect of low level laser therapy on the repair of bone defects grafted with inorganic bovine bone." Braz. Dent. J. [online], 2003, vol. 14, n.3 [cited Aug. 23, 2019], pp. 177-181.
Yaakobi, et al. "Promotion of Bone Repair in the Cortical Bone of the Tibia in Rats by Low Energy Laser (He—Ne) Irradiation", Calcified Tissue International, Oct. 1996, vol. 59, Issue 4, pp. 297-300.
Chang et al. "Therapeutic outcomes of low-level laser therapy for closed bone fracture in the human wrist and hand", Photomed Laser Surg. Apr. 2014;32(4):212-8.
Revolutionary metal vapour laser cuts bone and smartphone glass without burning it (last accessed Oct. 8, 2019).
Fávaro-Pípi, E., et al. "Comparative study of the effects of low-intensity pulsed ultrasound and low-level laser therapy on bone defects in tibias of rats," Lasers Med Sci (2010) 25: 727.
Junior, S. et al., "Computerized Morphometric Assessment of the Effect of Low-Level Laser Therapy on Bone Repair: An Experimental Animal Study" J Clin Laser Med Surg. Apr. 2002;20(2):83-7.
Ribeiro et al. "Low-Level Laser Therapy and Calcitonin in Bone Repair: Densitometric Analysis", International Journal of Photoenergy vol. 2012, Article ID 829587, 5 pages.
Moslemi, N. et al., "Laser-Assisted Osteotomy for Implant Site Preparation: A Literature Review," Implant Dent. Feb. 2017;26(1):129-136. doi: 10.1097/ID.0000000000000475.
Buchelt, M. , Kutschera, H. , Katterschafka, T. , Kiss, H. , Lang, S. , Beer, R. and Losert, U. (1994), Erb:YAG and Hol:YAG Laser Osteotomy: The Effect of Laser Ablation on Bone Healing. Lasers Surg. Med., 15: 373-381.
AboElsaad et al. "Effect of soft laser and bioactive glass on bone regeneration in the treatment of infra-bony defects (a clinical study)", Lasers in Medical Science, May 2009, vol. 24, Issue 3, pp. 387-395.
Medeiros et al. "Effects of laser vs ultrasound on bone healing after distraction osteogenesis" Angle Orthodontist, vol. 85, No. 4, 2015, pp. 555-561.
Erchonia Corporation study submitted to the FDA and given market clearance Jan. 2002.
Ozawa, et al., "Low-Energy Laser Irradiation Stimulates Bone Nodule Formation at Early Stages of Cell Culture in Rat Calvarial Cells", Bone, vol. 22, Issue 4, Apr. 1998, pp. 347-354.
Small et al. Observations of carbon dioxide laser and bone bur in the osteotomy of the rabbit tibia.; Journal of Oral Surgery (American Dental Association : 1965) Mar. 1, 1979, 37(3):159-166.
Oliveira et al. "Comparison of the effects of low-level laser therapy and low-intensity pulsed ultrasound on the process of bone repair in the rat tibia", Rev Bras Fisioter. 2011; 15(3):500-5.
Rheumatoid Arthritis.Rheumatoid arthritis overview. Causes of rheumatoid arthritis. Retrieved on Aug. 23, 2019 from http://www.low-level-laser-therapy-vityas.com/rheumatoid_arthritis-causes_of_rheumatoid_arthritis.html.
Rayan et al. Effects of rapid pulsed CO2 laser beam on cortical bone in vivo.; Lasers Surg Med. 1992;12(6):615-20.
Garavell-Freitas et al. "Low-power laser irradiation improves histomorphometrical parameters and bone matrix organization during tibia wound healing in rats" Journal of Photochemistry and Photobiology B: Biology, vol. 70, Issue 2, May-Jun. 2003, pp. 81-89.
How we treat What is Facture Healing? (http://www.stonehouseclinic.co.uk/fracture-healing.html) Sep. 30, 2019.
Batista, et al., "Laser Therapy Improves Healing of Bone Defects Submitted to Autologus Bone Graft" Photomedicine and Laser Surgery vol. 24, No. 1: Feb. 27, 2006.
Nelson, et. al., Mid-infrared erbium:YAG laser ablation of bone: The effect of laser osteotomy on bone healing; Lasers Surg. Med., 9: 362-374 (1989). doi:10.1002/lsm.1900090409 <https://doi.org/10.1002/lsm.1900090409>.
Kang, et. al., Investigations on laser hard tissue ablation under various environments,, Phys Med Biol. Jun. 21, 2008;53(12):3381-90. doi: 10.1088/0031-9155/53/12/021. Epub Jun. 3, 2008.
Barber et al. "Bone Regeneration and Repair" https://www.lzr7.com/research/bone-regeneration-and-repair/ (last accessed Oct. 8, 2019).

(56) References Cited

OTHER PUBLICATIONS

Pinheiro, et al., "Effect of low-power laser irradiation on the mechanical properties of bone fracture healing in rats," *Braz Dent J* (2003) 14(3): 177-181.
Li, et. al., Bone ablation with Er:YAG and CO2 laser: Study of thermal and acoustic effects, Lasers Surg. Med. (1992), 12: 79-85. doi:10.1002/lsm.1900120112 <https://doi.org/10.1002/lsm.1900120112>.
Cantwell et al., "Current trends in treatment of osteoid osteoma with an emphasis on radiofrequency ablation", European Radiology, Apr. 2004, vol. 14, Issue 4, pp. 607-617.
Bunion Laser Treatment: Is It Possible? (https://www.huffpost.com/entry/bunion-treatment_b_2988222) Original Apr. 3, 2013, printed Sep. 30, 2019.
Gertzbein, et al, "The effect of laser osteotomy on bone healing." Lasers Surg. Med., 1: pp. 361-373 (1981).
Ivanenko, et. al., Bone Tissue Ablation with sub-µs Pulses of a Q-switch CO2 Laser: Histological Examination of Thermal Side Effects, Lasers Med Sci (2002) 17: 258. https://doi.org/10.1007/s101030200038.
Friesen, et. al., "Laser Irradiation of Bone: II. Healing Response Following Treatment by CO2 and Nd:YAG Lasers." Journal of Periodontology, 70: 75-83 (1999).
Philip Gable "Bone Stimulation by Low Level Laser—A Theoretical Model for the Effects" (https://www.coldlasers.org/clinical-studies/bone-regeneration/) Printed Sep. 30, 2019.
Trelles, et al., "Bone fracture consolidates faster with low-power laser". Lasers Surg. Med., 7: 36-45 (1987).
Girard, et al., Effects of femtosecond laser irradiation on osseous tissues, Lasers Surg. Med. (2007), 39: 273-285. doi:10.1002/lsm.20466 <https://doi.org/10.1002/lsm.20466>.
Barushka et al. "Effect of low-energy laser (He—Ne) irradiation on the process of bone repair in the rat tibia", Bone, vol. 16, Issue 1, Jan. 1995, pp. 47-55.
Peter Ullrich "Laser Disc Decompression for Spinal Stenosis: Does it Work?" (https://www.spine-health.com/blog/laser-disc-decompression-spinal-stenosis-does-it-work) Published Jun. 30, 2007.
Ebrahimi, et al. The Influence of Low-Intensity Laser Therapy on Bone Healing J Dent (Tehran). 2012 Autumn; 9(4): 238-248.
Huang, et al., Micro-hole drilling and cutting using femtosecond fiber laser, Optical Engineering, 53(5) 051513 (2014). <https://doi.org/10.1117/1.OE.53.5.051513>.
Fritz-Ritson, et al., "Fractures", Advanced Therapeutic Centre, 2015.
Laser (https://www.sportswise.org.uk/laser) (last accessed Oct. 8, 2019).
Nuss et. al., Infrared laser bone ablation; Lasers Surg. Med., 8: 381-391. (1988) <https://doi.org/10.1002/lsm.1900080408>.
A Clinical Study of the Effectiveness for Mitigating Pain and Improving Range of Motion with the Erchonia Low-Level Laser on Minor Neck and Shoulder Pain: Jul.-Sep. 2000.
AboElSaad et al. "Effect of soft laser and bioactive glass on bone regeneration in the treatment of bone defects", Lasers in Medical Science, Jul. 2009, vol. 24, Issue 4, pp. 527-533.
Gebauer et al. "Thermal Ablation in Bone Tumors", Recent Results in Cancer Research, vol. 167 (2006).
Ueda & Shimizu, et al., Effects of Pulse Frequency of Low-Level Laser Therapy (LLLT) on Bone Nodule Formation in Rat Calvarial Cells, Journal of Clinical Laser Medicine & Surgery vol. 21, No. 5 (published online Jul. 8, 2004).
Khadra, M. "The effect of low level laser irradiation on implant-tissue interaction. In vivo and in vitro studies." Swedish Dental Journal: Supplement, Jan. 1, 2005 (172): 1-63.
Peavy, et. al., Comparison of cortical bone ablations by using infrared laser wavelengths 2.9 to 9.2 µm, Lasers Surg. Med. (1999), 25: 421-434. doi:3.0.CO;2-J"10.1002/(SICI)1096-9101(1999)25:5<421::AID-LSM9>3.0.CO;2-J <https://doi.org/10.1002/(SICI)1096-9101(1999)25:5<421::AID-LSM9>.

Favaro-Pipi, "Low-Level Laser Therapy Induces Differential Expression of Osteogenic Genes During Bone Repair in Rats" Photomedicine and Laser Surgery vol. 29 Issue 5: May 10, 2011.
Schmidt, et al. The use of CO2 laser in bone surgery; Magy Traumatol Orthop Helyreallito Seb. 1991;34(4):331-6.
Bossini, et al. "Low level laser therapy (830 nm) improves bone repair in osteoporotic rats: Similar outcomes at two different dosages," Experimental Gerontology, vol. 47, Issue 2, Feb. 2012, pp. 136-142.
Nicola et al. "Effect of low-power GaAlAs laser (660 nm) on bone structure and cell activity: An experimental animal study", Lasers in Medical Science 18(2): 89-974 Feb. 2003.
Bayat, et al., "The Effects of Low-Level Laser Therapy on Bone in Diabetic and Nondiabetic Rats", Photomedicine and Laser Surgery. vol. 27 Issue 5: Nov. 1, 2009.
Charlton et al,, Erbium-YAG and holmium-YAG laser ablation of bone Laser Med Sci (1990) 5: 365. https://doi.org/10.1007/BF02032593.
Tim, et al., "Low-level laser therapy enhances the expression of osteogenic factors during bone repair in rats" Lasers in Medical Science, Jan. 2014, vol. 29, Issue 1, pp. 147-156.
Foster, R. et al., "Bone and Soft Tissue Ablation", Semin Intervent Radiol. Jun. 2014; 31(2): 167-179.
Pinheiro, et al., "Biomodulatory Effects of LLLT on Bone Regeneration", Laser Therapy, 2000 vol. 13 Issue 1, pp. 73-79.
Wet bone ablation with mechanically Q-switched high-repetition-rate CO2 laser (last accessed Oct. 8, 2019).
Pires-Oliveira, et al., "Laser 904 nm action on bone repair in rats with osteoporosis", Osteoporos Int. Dec. 2010;21(12):2109-14.
Pretel, H., et al. Effect of low-level laser therapy on bone repair: Histological study in rats. Lasers Surg. Med., 39: 788-796 (2007).
Bossini, et al., "Biosilicate® and low-level laser therapy improve bone repair in osteoporotic rats." J Tissue Eng Regen Med. Mar. 2011;5(3):229-37.
Rupprecht, et al., Sensor-based laser ablation fortissue specific cutting: an experimental study, Lasers Med Sci (2004) 19: 81. https://doi.org/10.1007/s10103-004-0301-2.
Ozdemir, et al., "The clinical efficacy of low-power laser therapy on pain and function in cervical osteoarthritis." Clin Rheumatol. 2001;20(3):181-4.
Lirani-Galvao, et al., "Comparative Study of How Low-Level Laser Therapy and Low-Intensity Pulsed Ultrasound Affect Bone Repair in Rats," Photomedicine and Laser Surgery. vol. 24 Issue 6: Jan. 2, 2007.
Ekim, et al., "Effect of low level laser therapy in rheumatoid arthritis patients with carpal tunnel syndrome: A placebo controlled study" Swiss Med Wkly. Jun. 16, 2007;137(23-24):347-52.
Papadaki, et. al., Vertical ramus osteotomy with Er:YAG laser: a feasibility study, International Journal of Oral and Maxillofacial surgery,International Journal of Oral and Maxillofacial Surgery vol. 36, Issue 12 </science/journal/09015027/36/12>, Dec. 2007, pp. 1193-1197.
Asada et al. "Clinical application of GaAlAs 830 nm diode laser in treatment of rheumatoid arthritis", Laser Therapy 3(2):77-82 • Jan. 1991.
Kessler et al., "Use of Er:YAG Laser to Improve Osseointegration of Titanium Alloy Implants—A Comparison of Bone Healing" International Journal of Oral & Maxillofacial Implants . May/Jun. 2006, vol. 21 Issue 3, p. 375-379.
Nicola et al., "Effect of low-power GaAlAs laser (660 nm) on bone structure and cell activity: an experimental animal study" Lasers Med Sci (2003) 18: 89.
Tulea et al., "Laser cutting of bone tissue under bulk water with a pulsed ps-laser at 532 nm" J. of Biomedical Optics, 20(10) 105007 (2015). <https://doi.org/10.1117/1.JBO.20.10.105007>.
Pinheiro and Gerbi, "Photoengineering of Bone Repair Processes", Photomedicine and Laser Surgery, vol. 24, No. 2 (published online May 17, 2006).
Matsumoto, et al., "Low-level laser therapy modulates cyclo-oxygenase-2 expression during bone repair in rats," Lasers Med Sci (2009) 24: 195.

(56) References Cited

OTHER PUBLICATIONS

Gordjestani, et al., "Infrared laser and bone metabolism: A pilot study" International Journal of Oral and Maxillofacial Surgery vol. 23, Issue 1, Feb. 1994, pp. 54-56.
Orthopedic Surgery Technology, DocShop, updated Sep. 6, 2017.
Garbi, et al., "Infrared Laser Light Further Improves Bone Healing When Associated with Bone Morphogenic Proteins: An in Vivo Study in a Rodent Model",Photomedicine and Laser Surgery, vol. 26 Issue 1, Feb. 4, 2008.
Spencer et al. Effective laser ablation of bone based on the absorption characteristics of water and proteins; J Periodontol. Jan. 1999;70(1):68-74.
Buchelt, et al., "High power Ho:YAG laser ablation of intervertebral discs: Effects on ablation rates and temperature profile", Lasers in Surgery and Medicine, vol. 16, Issue, pp. 179-183 (first published 1995).
Liu, et al., Ablation of femural bone with femtosecond laser pulses—a feasibility study, M. Lasers Med Sci (2007) 22: 171. https://doi.org/10.1007/s10103-006-0424-8.
Choy, et al., "Percutaneous Laser Disc Decompression: A New Therapeutic Modality", Spine: Aug. 1992, vol. 17, Issue 8, pp. 949-956.
Gonzalez et al., Comparison of the erbium-yttrium aluminum garnet and carbon dioxide lasers for in vitro bone and cartilage ablation The Laryngoscope, 100: 14-17 (1990).
Casper, et al. "Results of a clinical trial of the holmium:YAG laser in disc decompression utilizing a side-firing fiber: A two-year follow-up", Lasers in Surgery and Medicine, vol. 19, Issue 1, 1996, pp. 90-96.
Zeitouni J, et al. "The effects of the Er:YAG laser on trabecular bone micro-architecture: Comparison with conventional dental drilling by micro-computed tomographic and histological techniques [version 1; peer review: 2 approved]." *F1000Research* 2017, 6:1133 (<https://doi.org/10.12688/f1000research.12018.1>).
Buchelt et al., "Fluorescence guided excimer laser ablation of intervertebral discs in vitro", Lasers in Surgery and Medicine, vol. 11, Issue 3, 1991, pp. 280-286.
Mortensen, et al., Femtosecond laser bone ablation with a high repetition rate fiber laser source; Biomed Opt Express. Jan. 1, 2015; 6(1): 32-42.
El Montaser et al. "Effect of low-level laser therapy on bone repair: a randomized controlled experimental study", Lasers in Surgery and Medicine, vol. 21, Issue 3, 1997, pp. 255-261.
Lo, et. al., Femtosecond Plasma Mediated Laser Ablation Has Advantages Over Mechanical Osteotomy of Cranial Bone, Lasers Surg Med. Dec. 2012;44(10):805-14. doi: 10.1002/lsm.22098. Epub Nov. 26, 2012.
Islam et al., "Effect of low level laser (Diode 830 NM) therapy on-Human Bone Regeneration" J. Biotechnology Biomater 2016, 6:3(suppl).
Walsh et al., Er:YAG laser ablation of tissue: Effect of pulse duration and tissue type on thermal damage; Lasers Surg. Med., 9: 314-326 (1989) doi:10.1002/lsm.1900090403 <https://doi.org/10.1002/lsm.1900090403>.
Clayman, et al., "Healing of continuous-wave and rapid superpulsed, carbon dioxide, laser-induced bone defects," Journal of Oral Surgery (American Dental Association : 1965) Dec. 1, 1978, 36(12):932-937.
Frentzen, et al., Osteotomy with 80-µs $CO_2$ laser pulses—histological results, Lasers Med Sci (2003) 18: 119. https://doi.org/10.1007/s10103-003-0264-8.
Kamali, et al, "The therapeutic effect of low-level laser on repair of osteochondral defects in rabbit knee," Journal of Photochemistry and Photobiology B: Biology, vol. 88, Issue 1, Jul. 27, 2007, pp. 11-15.
Forrer, et al., Bone-ablation mechanism using $CO2$ lasers of different pulse duration and wavelength, Applied Physics B; Feb. 1993, vol. 56, Issue 2, pp. 104-112.

Liu, et al., "Effect of Lower-Level Laser Therapy on Rabbit Tibial Fracture", Photomedicine and Laser Surgery. vol. 25 Issue 6: Dec. 25, 2007.
Pinheiro, et al., "Infrared Laser Light Further Improves Bone Healing When Associated with Bone Morphogenetic Proteins and Guided Bone Regeneration: An in Vivo Study in a Rodent Model" Photomedicine and Laser Surgery, vol. 26, No. 2 (published online Apr. 28, 2008).
Tajali, et al., "Effects of low power laser irradiation on bone healing in animals: a meta-analysis", Journal of Orthopaedic Surgery and Research 201, 5:1 (first published 1992).
Gottlob, et al., "Holmium:YAG laser ablation of human intervertebral disc: Preliminary evaluation", Lasers in Surgery and Medicine, vol. 12, Issue 1, 1992, pp. 86-91.
Bossini, et al., "Low level laser therapy (830nm) improves bone repair in osteoporotic rats: similar outcomes at two different dosages." Exp Gerontol. Feb. 2012;47(2):136-42.
Min, et al. "Quantitative determination of ablation in weight of lumbar intervertebral discs with Holmium:YAG laser", Lasers in Surgery and Medicine, vol. 18, Issue 2, 1996, pp. 187-190.
Sidorov, et al. "The interauricular laser therapy of rheumatoid arthritis" Vopr Kurortol Fizioter Lech Fiz Kult. May-Jun. 1999;(3):35-43.
Daniel S. Choy, "Percutaneous Laser Disc Decompression (PLDD): Twelve Years' Experience with 752 Procedures in 518 Patients" Journal of Clinical Laser Medicine & Surgery, vol. 16, issue 6, Apr. 29, 2009.
Guzzardella, et al. "Osseointegration of endosseous ceramic implants after postoperative low-power laser stimulation: an in vivo comparative study", Clinical Oral Implants Research, vol. 14 Issue 2, Apr. 2003, pp. 226-232.
El Montaser et al. "Pattern of healing of calvarial bone in the rat following application of the erbium-YAG laser", Lasers in Surgery and Medicine, vol. 21, Issue 3, 1997, pp. 255-261.
Pinheiro, et al., "Bone repair following bone grafting hydroxyapatite guided bone regeneration and infra-red laser photobiomodulation: a histological study in a rodent model" Lasers in Medical Science, Mar. 2009, vol. 24, Issue 2, pp. 234-240.
Batistia et al. "Low-level laser therapy on bone repair: is there any effect outside the irradiated field?", Lasers in Medical Science, Jul. 2015, vol. 30, Issue 5, pp. 1569-1574.
Ailioaie, et al., "Beneficial Effects of Laser Therapy in the Early Stages of Rheumatoid Arthritis Onset", Laser Therapy, 1999 vol. 11, Issue 2, pp. 79-87.
Scalize et al. "Low-level laser therapy improves bone formation: stereology findings for osteoporosis in rat model", Lasers Med Sci. Jul. 2015; 30(5): 1599-607.
Guzzardella, et al. "Low-Power Diode Laser Stimulation of Surgical Osteochondral Defects: Results After 24 Weeks" Artificial Cells, Blood Substitutes, and Biotechnology, vol. 29, (2001), Issue 3 pp. 235-244.
Shakouri, et al. "Effect of low-level laser therapy on the fracture healing process," Lasers Med Sci (2010) 25: 73.
Goldman, et al., "Laser therapy of rheumatoid arthritis," Lasers Surg Med. 1980;1(1):93-101.
Fernandes, et al., "Effects of low-level laser therapy on the expression of osteogenic genes related in the initial stages of bone defects in rats", Journal of Biomedical Optics, vol. 18, Issue 3 (Mar. 2013).
Ribeiro, et al., "Low-level laser therapy improves bone repair in rats treated with anti-inflammatory drugs" J Oral Rehabil. Dec. 2008;35(12):925-33.
Barber, et al., "Advances in Laser Therapy for Bone Repair" Laser Therapy (2001), vol. 13, pp. 80-85.
Trauner, "Pulsed holmium:yttrium-aluminum-garnet (Ho:YAG) laser ablation of fibrocartilage and articular cartilage" The American Journal of Sports Medicine, vol. 18, No. 3 (1990).
Coppi "Research: Could laser treatment help to fix osteoporosis bone weakening?" Jun. 15, 2015.
Perry "Understand your bone spur treatment options" (Last Accessed Oct. 8, 2019).
Yin "Controlled Fiber Laser Bone Ablation Using Inline Coherent Imaging" (Last accessed Sep. 2015).

(56) References Cited

OTHER PUBLICATIONS

Laser Ablation Shows Benefit for Tumors Near the Spine (last Accessed May 6, 2015).

Shaofang et al., "First Study on Laser Bone Ablation System at the Skull Base for Micro Surgery Based on Vision Navigation" Proceedings of the 26th Chinese Control Conference on Oct. 15, 2017.

Schnee "Why Does Cold Laser Therapy Help Relieve 'Bone on Bone' Knee Pain?" (last accessed Feb. 1, 2011).

Erchonia XLR8 Laser Granted FDA Clearance for Pain Treatment (https://www.erchonia.com/erchonia-xlr8-laser-granted-fda-clearance-for-pain-treatment/) Printed Oct. 1, 2019.

Buchelt, et al., "Erb:YAG and Hol:YAG laser ablation of meniscus and intervertebral discs", Lasers in Surgery and Medicine, vol. 15, Issue 4, pp. 373-381 (1994).

Shimokita et al., "Evaluation of bone carbonization by CO2 laser osteotomy" (last accessed Dec. 9, 2008).

Ivanenko "In vivo animal trials with a scanning CO2 laser osteotome" Lasers in Surgery and Medicine, vol. 37, Issue 2, pp. 144-148, Aug. 30, 2005.

Akyol et al., "Histologic Evaluation of the Effects of Er:YAG Laser on Bone Ablation", The Journal of Contemporary Dental Practice, vol. 10, Issue 5, E065-72 (2009).

Burgner-Kahrs, et al., "Robot Assisted Laser Bone Ablation" International Conference on Advanced Robotics, Jul. 2009.

Bayat et al. "Comparison of the in vitro effects of low-level laser therapy and low-intensity pulsed ultrasound therapy on bony cells and stem cells" Progress in Biophysics and Molecular Biology, Nov. 2017, vol. 33, pp. 36-48.

Nees, "Facet thermal ablation—minimally invasive surgery for facet arthritis" (last accessed Oct. 8, 2019).

Ivanenko et al., "Hard tissue ablation with a mechanically Q-switched CO2 laser", Thermal Therapy, Laser Welding and tissue Interaction, vol. 3565, (last accessed Jan. 4, 1999).

Giraud et al., "Bone cutting", Clinical Physics and Physiological Measurement, vol. 12, Issue 1 (last Accessed Oct. 8, 1991).

Khader et al., :Ultrashort Laser Ablation of Cortical Bone: Literature Review and Experimental Evaluation (last Accessed Oct. 2013).

Troedhan et al. "Cutting bone with drills, burs, lasers and piezotomes: A comprehensive systematic review and recommendations for the clinician", International Journal of Oral and Craniofacial Science, vol. 3, Issue 2, pp. 020-033, Aug. 14, 2017.

Schwab et al., "Bone ablation using ultrashort laser pulses. A new technique for middle ear surgery", Laryngo-Rhino-Otologie, vol. 83, issue 4, pp. 219-225, Apr. 2004.

* cited by examiner

| Feature | Min. value | Nominal value | Max. value | (units) |
|---|---|---|---|---|
| Wavelength | 3 | 9.3 | 11 | μm |
| Pulse length | 5 | 100 | 10,00 | μsec |
| Pulse energy | 10 | 1,000 | 100,000 | mJ |
| Fluence at focus | 1 | 20 | 100 | J/cm$^2$ |
| Waist diameter | 50 | 250 | 500 | μm |
| Taper angle relative to normal to treatment surface | 0 | 15 | 30 | deg |
| Depth of treatment distance about waist | 25 | 50 | 100 | mm |
| Distance of surface to be treated from hand piece tip | 10 | 50 | 100 | mm |
| Pulse repetition rate | 0.10 | 0.5 to 2 | 4 | kHz |
| Laser beam spot size diameter | 200 | 500 | 10,000 | μm |
| Hard tissue removal rate | 0.5 | 1 | 3 | g/sec |
| Volumetric removal rate | 0.17 | 0.5 | 1 | cm$^3$/sec |
| Treatment time | 2 | 60 | 180 | secs |
| Laser beam angle of incidence | 0 | 30 | 90 | degrees |
| Fluidic flow angle of incidence | 0 | 65 | 90 | degrees |
| Duty cycle | 0.01 | 20 | 40 | percent |
| Energy profile | Top Hat, Gaussian, Donut, Random | | | N/A |
| Condition of tooth | Wet, Dry, Clean Cut, Sterilized, Fractured | | | N/A |

FIG. 3

| Feature | Min. value | Nominal value | Max. value | (units) |
|---|---|---|---|---|
| Peak power output of the laser | 300 | 500 | 10,000 | W |
| Peak power input of the laser | 1,000 | 20,000 | 100,000 | W |
| Average power output of the laser | 30 | 50 | 1,000 | W |
| Average power input of the laser | 100 | 2,000 | 10,000 | W |
| Peak power per pulse | 300 | 500 | 10,000 | W |
| Average power per pulse | 30 | 50 | 1,000 | W |
| Input voltage of power supply | 600 | 1,000 | 10,000 | V |
| Input current of power supply | 30 | 100 | 500 | A |
| DC output voltage of power supply | 48 | 144 | 288 | V |
| DC output current of power supply (current delivered to capacitor bank) | 100 | 1,000 | 10,000 | A |
| Output voltage of capacitor bank | 48 | 144 | 288 | V |
| Output voltage of individual capacitors in capacitor bank | 48 | 144 | 288 | V |
| Capacitance of individual capacitors in capacitor bank | 68,000 | 150,000 | 500,000 | μF |
| Number of capacitors in capacitor bank | 4 | 100 | 500 | |
| Output current of capacitor bank | 100 | 1,000 | 10,000 | A |
| Change in laser temperature from ambient to steady state | 1 | 10 | 40 | °C |
| Rate of change of laser temperature | 0.001 | 0.2 | 25 | °C/min |

FIG. 4

| Feature | Min. value | Nominal value | Max. value | (units) |
|---|---|---|---|---|
| Energy profile | Top Hat, Gaussian, Donut, Random | | | N/A |
| Condition of tissue | Wet, Dry, Clean Cut, Sterilized, Fractured | | | N/A |
| Rate at which galvos can adjust mirrors | 2500 | 100,000 | 500,000 | steps per second |
| Number of mirrors | 1 | 2 | 3 | N/A |
| Displacement of the laser at focus due to an adjustment of a mirror | 250 | 2,000 | 10,000 | um |
| Shape of treatment area | Triangle, Square, Rectangle, Hexagon, Other polygons, Circle, Oval | | | N/A |
| Size of treatment area | 15,000 | 100,000 | $2.25 \times 10^6$ | $um^2$ |
| Depth of treatment area | 50 | 20000 | 10000 | um |
| Length of a segment of a perimeter that can be programmed as the treatment area | 500 | 150,000 | $2.25 \times 10^6$ | um |
| Pattern of scanning | Random, Raster, Circular, Any Pattern | | | N/A |
| Angle of the tapering portion of the hand piece (from galvos to 90 deg. turning optic) | 5 | 20 | 45 | degrees |
| Focal length of the first lens (upstream of galvos) | 2 | 7.5 | 10 | cm |
| Angle at which the turning optic can change the angle of the incident laser beam | 45 | 90 | 135 | degrees |

FIG. 6

| Feature | Min. value | Nominal value | Max. value | (units) |
|---|---|---|---|---|
| Pressure of the coolant | 0.1 | 40 | 100 | psi |
| Gas pressure | 0.1 | 40 | 100 | psi |
| Liquid pressure | 0.1 | 40 | 100 | psi |
| Volumetric flow rate of the coolant | 10 | 100 | 1,000 | mm$^3$/min |
| Gas volumetric flow rate | 10 | 100 | 1,000 | mm$^3$/min |
| Liquid volumetric flow rate | 10 | 100 | 1,000 | ml/min |
| Percentage of liquid in fluid | > 0 | 50 | < 100 | N/A |
| Type of flow | continuous, bursts, alternating | | | N/A |
| Frequency of bursts | 0.1 | 1 | 10 | Hz |
| Duration of a burst | 0.1 | 100 | 1000 | ms |
| Fluid type | air and water mix, water may have salt | | | N/A |
| Examples of additives | peroxide, medications, pigments, minerals | | | N/A |
| Number of nozzles | 1 | 4 | 10 | N/A |
| Pattern of nozzles | square, circle, ellipse | | | N/A |
| Angular range within which a nozzle can be oriented | 0 | 45 | 90 | degrees |
| Nozzle orifice diameter | 4 | 8 | 12 | mm |
| Size of impinging area corresponding to one nozzle | 1.35 | 5 | 10 | mm$^2$ |
| Shape of impinging area corresponding to one nozzle | circle | | | N/A |
| Flow pattern | droplet, column, mist | | | |
| Stand off between the nozzles and the surface of the tissue | 10 | 50 | 100 | mm |

FIG. 8

LASER SYSTEM FOR SURGICAL APPLICATIONS

CROSS-REFERENCE TO RELATED APPLICATIONS

This application claims the benefit of priority to U.S. Provisional Patent Application No. 62/651,987 entitled "Laser System for Surgical Applications," filed on Apr. 3, 2018 and to U.S. Provisional Patent Application No. 62/651,982 entitled "Laser System for Surgical Applications," filed on Apr. 3, 2018, the contents of both of which are incorporated herein by reference in their entireties.

TECHNICAL FIELD

This invention relates generally to laser-based treatment systems and more particularly to using lasers in surgical applications for selectively treating hard and soft tissues, including bones, skin, and connective tissue.

BACKGROUND

The cutting and removal of tissue (e.g., hard tissue such as bone) is necessary in a wide range of surgical applications. Typically, the tissue is cut with saws, drills, and other rudimentary tools similar to those used for cutting other hard materials with mechanical shearing forces. While such tools can be effective at cutting through bone, they present numerous drawbacks for surgeons and patients. For example, conventional tools generally include a large blade that can be difficult to locate in close proximity to the desired bone. Saws, drills, and cautery tools currently used for surgical procedures cut through bone by frictional tearing and shearing, which produces significant tissue damage that compromises patient recovery. The unavoidable surface and subsurface damage contributes to severe postoperative pain. In vivo studies demonstrate that the cutting process also generates substantial frictional heat, leading to osteonecrosis and subsequent resorption of necrotic bone. Established soft tissue cauterization methods used to quell blood loss compound the recovery burden for patients, as these tools burn tissue in order to coagulate blood vessels. Thus, an improved technique for cutting tissues such as bones is desired.

One alternative cutting technique is the use of lasers, which has previously been explored for the cutting of dental tissue. The outermost layer of a tooth is enamel which is the hardest and forms a protective layer for the rest of the tooth. The middle and bulk of the tooth is made up of the dentin and the innermost layer is the pulp. Research has taken place to define laser parameters that allow the enamel and dentin of a tooth to be removed, drilled, contoured or conditioned, without heating the pulp. High energy density pulses were initially used, but these pulses were found to damage the tooth pulp or soft tissue, so lower energy pulse configurations were explored. It has been discovered that certain $CO_2$ lasers having a peak power output between 10 W and 300 W are effective in cutting dental tissue while avoiding damage to the pulp.

There remains a need for a laser cutting system adapted to treat tissues of various types other than tissues found in the dental cavity (e.g., to perform various surgical procedures).

SUMMARY

Accordingly, the present disclosure relates to a laser system adapted for treating tissue throughout the body, e.g., bone, skin, connective tissue, etc. Example procedures performed using the system can include cartilage excision for joint preparation/arthroplasty, bone removal, grafting (e.g., for femur/humerus surgery), hip arthroplasty (e.g., reaming the acetabulum), insertion and stabilization of bone prostheses, etc. Various embodiments of the system include improved features over conventional laser treatment systems designed primarily for the treatment of dental tissue. In some instances, the system can perform treatment with a polarized laser beam, which exhibits improved cutting properties over conventional laser beams. In addition, the system can include high definition imagers for real-time, on-axis visualization and spatial measurement of the surgical region. In some instances, the surgical region can be imaged with a polarized light beam, which can enable improved viewing of nerves and other anatomical structures during treatment.

In one aspect, the invention relates to a laser-based treatment system for treating a tissue. The system can include a laser source for generating a laser beam having a wavelength in a range from 9 μm to 11 μm and a peak output power of at least 500 W; a hand piece optically connected to the laser source and including (i) an optical component for directing the laser beam at a treatment surface of the tissue and (ii) an imaging system for imaging the treatment surface; and a controller for controlling at least one parameter of the laser-based treatment system.

In some embodiments of the above aspect, the laser-based treatment system is adapted to ablate the tissue and/or assist with insertion of a bone prosthesis. In some instances, the imaging system is adapted to provide guidance and visualization of alignment for insertion of the bone prosthesis. The tissue can be a hard tissue and, in some cases, the laser beam removes the hard tissue at a rate in a range from 0.5 g/sec to 5 g/sec. In some instances, the tissue also includes a soft tissue. The tissue can include bone, muscle, tendon, cartilage, vascular, nerves, mucosa, and/or skin. In some instances, the laser-based treatment system is adapted to excise cartilage and/or bone in a joint preparation procedure, a femur osteotomy procedure, and/or a humerus osteotomy procedure. In some instances, the laser-based treatment system is adapted to prepare and/or expose joint cartilage.

In various embodiments, the laser source includes a $CO_2$ laser source. In other instances, the laser source includes a He—Ne laser source, an argon laser source, a UV laser source, an Er-YAG laser source, and/or an excimer laser source. In various instances, the laser beam can include: a pulse length in a range from 5 μs to 1,000 μs, a pulse energy in a range from 10 mJ to 100,000 mJ, and/or a pulse repetition rate of 0.1 kHz to 4 kHz. In some cases, the optical component includes a galvanometer and/or a turning mirror.

In various embodiments, the imaging system includes a high-definition imaging system adapted to generate images (e.g., digital images) of the treatment surface having a resolution of at least 10,000 ppi (i.e., pixels per inch). The system can further include a digital storage medium to store the digital images. In some instances, the imaging system includes a 3D imaging system which, in some cases, includes at least two sensors. The imaging system can be substantially symmetrical about a cutting axis on the treatment surface. In other cases, the imaging system is configured at different angles (e.g., in a range from 0-45 degrees) for desired imaging capabilities. In some cases, the imaging system includes a CMOS/CCD sensor. In some cases, the imaging system includes a polarized illumination source and a linear polarizer (e.g., half wave plate). The linear polarizer can be adapted to translate and/or rotate to alter a contrast of images received from the treatment surface. In other cases, the imaging system can include polarization based on optical coherence tomography, polarized Raman spectroscopy, and/or polarization microscopy.

In various embodiments, the laser-based treatment system further includes a cooling unit for directing a pressurized fluid at the treatment surface. In some cases, a volumetric flow rate of the pressurized fluid is in a range from 10 mm$^3$/min to 1,000 mm$^3$/min. In some cases, the pressurized fluid is directed in bursts, e.g., at a frequency in a range from 0.1 Hz to 10 Hz. The duration of each burst can be in a range from 100 ms to 10,000 ms. The pressurized fluid can be a pressurized gas, a pressurized liquid, and/or combinations thereof. In some instances, the system can further include a linear polarizer and/or a circular polarizer adapted to polarize the laser beam. Both the linear polarizer (e.g., a half wave plate) and the circular polarizer (e.g., a quarter wave plate) can be mounted within the hand piece. In some configurations, the linear polarizer is mounted within the hand piece proximate a galvanometer and the circular polarizer is mounted within the hand piece proximate an outlet orifice. The laser beam can be linearly polarized, circularly polarized, and/or elliptically polarized. In some instances, the circular polarizer is rotatable so as to alter an output power of the laser beam exiting the hand piece.

In another aspect, the invention relates to a method of treating a tissue using a laser-based treatment system. The method can include the steps of generating a laser beam having a wavelength in a range from 9 µm to 11 µm and a peak output power of at least 500 W; optically connecting the laser source to a hand piece, the hand piece including (i) an optical component for directing the laser beam at a treatment surface of the tissue and (ii) an imaging system for imaging the treatment surface; and controlling at least one parameter of the laser-based treatment system.

In various embodiments, the method can further include the steps of ablating the tissue, inserting a bone prosthesis, and/or using the laser-based treatment system to provide guidance and visualization of alignment for insertion of the bone prosthesis. The tissue can be hard tissue. In some cases, the method can further include removing the hard tissue at a rate in a range from 0.5 g/sec to 5 g/sec. In some instances, the tissue also includes a soft tissue. The tissue can include bone, muscle, tendon, and/or cartilage. In some instances, the method further includes excising cartilage and/or bone in a joint preparation procedure, a femur osteotomy procedure, and/or a humerus osteotomy procedure. In some instances, the method can further include preparing joint cartilage and/or exposing joint cartilage.

In various embodiments, the laser source includes a $CO_2$ laser source. In other instances, the laser source includes a He—Ne laser source, an argon laser source, a UV laser source, an Er-YAG laser source, and/or an excimer laser source. In various instances, the laser beam can include: a pulse length in a range from 5 µs to 1,000 µs, a pulse energy in a range from 10 mJ to 100,000 mJ, and/or a pulse repetition rate of 0.1 kHz to 4 kHz. In some cases, the optical component includes a galvanometer and/or a turning mirror.

In various embodiments, the imaging system includes a high-definition imaging system adapted to generate images (e.g., digital images) of the treatment surface having a resolution of at least 10,000 ppi. The method can further include storing the digital images in a digital storage medium. In some instances, the imaging system includes a 3D imaging system which, in some cases, includes at least two sensors. The imaging system can be substantially symmetrical about a cutting axis on the treatment surface. In some cases, the imaging system includes a CMOS/CCD sensors. In some cases, the imaging system includes a polarized illumination source and a linear polarizer (e.g., half wave plate). The method can further include translating and/or rotating the linear polarizer to alter a contrast of images received from the treatment surface.

In various embodiments, the method further includes directing a pressurized fluid at the treatment surface. In some cases, a volumetric flow rate of the pressurized fluid is in a range from 10 mm$^3$/min to 1,000 mm$^3$/min. In some cases, the pressurized fluid is directed in bursts, e.g., at a frequency in a range from 0.1 Hz to 10 Hz. The duration of each burst can be in a range from 100 ms to 10,000 ms. The pressurized fluid can be a pressurized gas, a pressurized liquid, and/or combinations thereof. In some instances, the method further includes polarizing the laser beam using at least one of a linear polarizer and a circular polarizer. Both the linear polarizer (e.g., a half wave plate) and the circular polarizer (e.g., a quarter wave plate) can be mounted within the hand piece. In some configurations, the linear polarizer is mounted within the hand piece proximate a galvanometer and the circular polarizer is mounted within the hand piece proximate an outlet orifice. The laser beam can be linearly polarized, circularly polarized, and/or elliptically polarized. In some instances, the method further includes rotating the circular polarizer so as to alter an output power of the laser beam exiting the hand piece.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 3 is a chart providing example laser parameter values, according to various embodiments;

FIG. 4 is a chart providing example power parameter values, according to various embodiments;

FIG. 6 is a chart providing example parameter values related to the beam guidance system, according to various embodiments;

FIG. 8 is a chart providing example cooling parameter values, according to various embodiments;

DETAILED DESCRIPTION

Embodiments of the present invention relate to a laser-based system for treating a variety of hard and soft tissues for use in performing a wide range of surgical procedures. This disclosure will often describe the treatment system as being used for treating tissues outside of the dental cavity, e.g., bones (other than teeth), skin, connective tissue (e.g., within joints), etc. However, in various embodiments, the system described herein can also be used for the treatment of tissue within the oral cavity.

Figure 1:
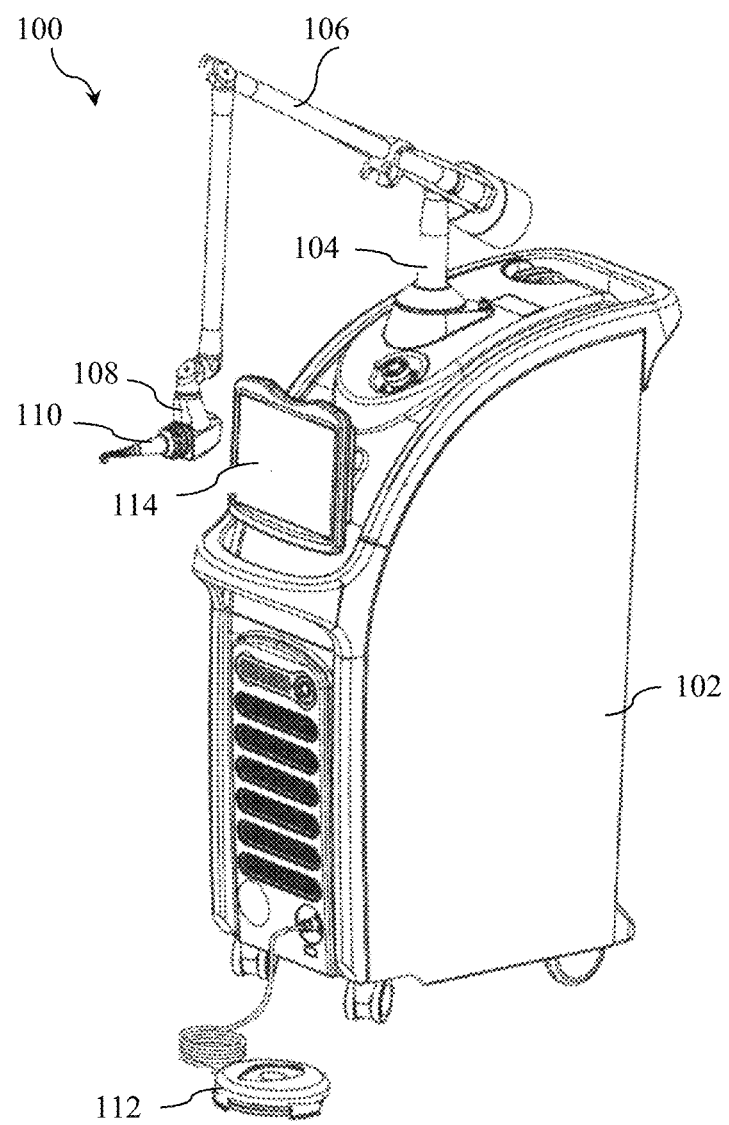
FIG. 1 is a schematic perspective view of a surgical laser treatment system, according to various embodiments.

With reference to FIG. 1, in an exemplary laser treatment system 100, a laser beam from a laser source 102 is directed into an articulating arm launch 104. The beam is further directed into an articulated arm 106, and exits therefrom through an end opposite the launch 104. A main chamber 108 includes a fixed or an interchangeable hand piece 110. A foot pedal 112 can control aspects of the system 100. The foot pedal 112 is illustrative only. In general, control of one or more parameters of the systems 100 can be achieved using any suitable switch or variable input device, such as a mouse, keyboard, joy stick, touch screen panel, slider switch, etc. The system 100 can also include a monitor/user interface 114 that can receive input from the user and/or display images to the user.

Figure 2:
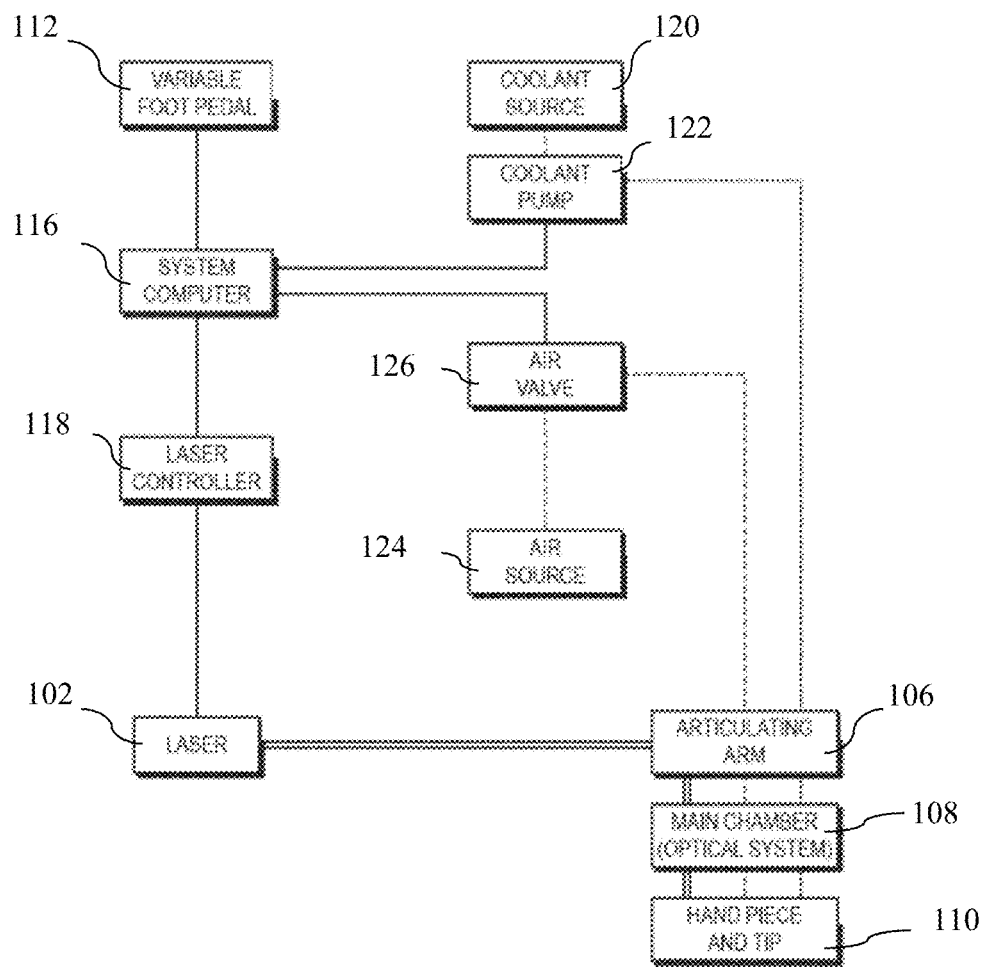
FIG. 2 is a schematic diagram showing various components of the surgical laser treatment system, according to various embodiments.

With reference to FIG. 2, the position of the foot pedal 112 can be varied, for example, to control a computer 116, which in turn can control a laser controller 118, so as to control the operation of the laser source 102 and/or associated subsystems. Using the foot pedal 112 (or any input device, in general), the laser source 102 may be turned on/off, and/or other system parameters such as the pulsing of the laser beam, intensity thereof, rate of flow and/or pressure of a coolant, etc., may be controlled. The laser beam generally passes through an optical system (e.g., mirrors that reflect the laser beam at angles, e.g., 45°) within the articulating arm 106 and/or main chamber 108 to a tip of the hand piece 110. The hand piece 110 can rotate in certain embodiments to provide flexibility in positioning the tip and accessibility to tissues that are difficult to target. A coolant from a coolant source 120 may be supplied to the hand piece 110 via the articulating arm 106 using a computer-controlled coolant pump 122. Pressurized air from an air source 124 may also be supplied to the hand piece 110 via the articulating arm 106 using a computer-controlled valve 126. The pressurized air may be used in combination with the coolant to generate a cooling mist and/or may be used to protect various components located in the hand piece 110. In some instances, the laser beam is invisible to the human eye and another marking beam coincident with the laser beam and having a visible wavelength can also be directed to the treatment site to assist in determining the location of the laser beam. In other instances, the articulated arm 106 includes a waveguide (e.g., fiber based) through which the laser beam propagates and is delivered through the hand piece 110 onto the target area.

In various embodiments, the laser source 102 can generate a $CO_2$ laser beam having a wavelength in the range of 3 μm-11 μm. In other instances, the laser source 102 can generate a laser beam having a wavelength in a range from 400 nm to 1 μm, which includes both visible light wavelengths (e.g., 400-700 nm) and near infrared light wavelengths (e.g., 700 nm-1 μm). The laser beam can be delivered as either a single or multiple discrete wavelengths or as a broadband range of wavelengths. The laser beam can be delivered in either a continuous wave or a pulsed mode. In the pulsed mode, the laser beam can include a train of laser pulses having an energy of 10 mJ-100,000 mJ per pulse, a pulse width of 5 μsec-1,000 μsec, and a pulse repetition rate of the laser pulses 0.1 kHz-4 kHz. Additional example parameters of the laser are shown in FIG. 3.

As presented in the laser power parameter chart of FIG. 4, the peak power output of the laser (either CW or pulsed) can be in a range from 300 W to 10,000 W and the average power output of the laser (either CW or pulses) can be in a range from 30 W to 1,000 W. In various instances, the peak power input can be in a range from 1,000 W to 100,000 W and the average power input can be in a range from 100 W to 10,000 W. Lasers capable of achieving such high power output have been too large to reasonably house within many hospital operating rooms. In addition, such lasers are not suitable for dental applications, because of the detrimental melting/charring effect on the pulp. However, many tissues in the body do not have the same sensitivities and thus can be treated with these higher power laser beams, which makes certain cutting activities (e.g., grafting of the femur, scoping a knee, etc.) feasible that were not practical with conventional systems. Additional example power parameters are shown in FIG. 4.

Figure 5:
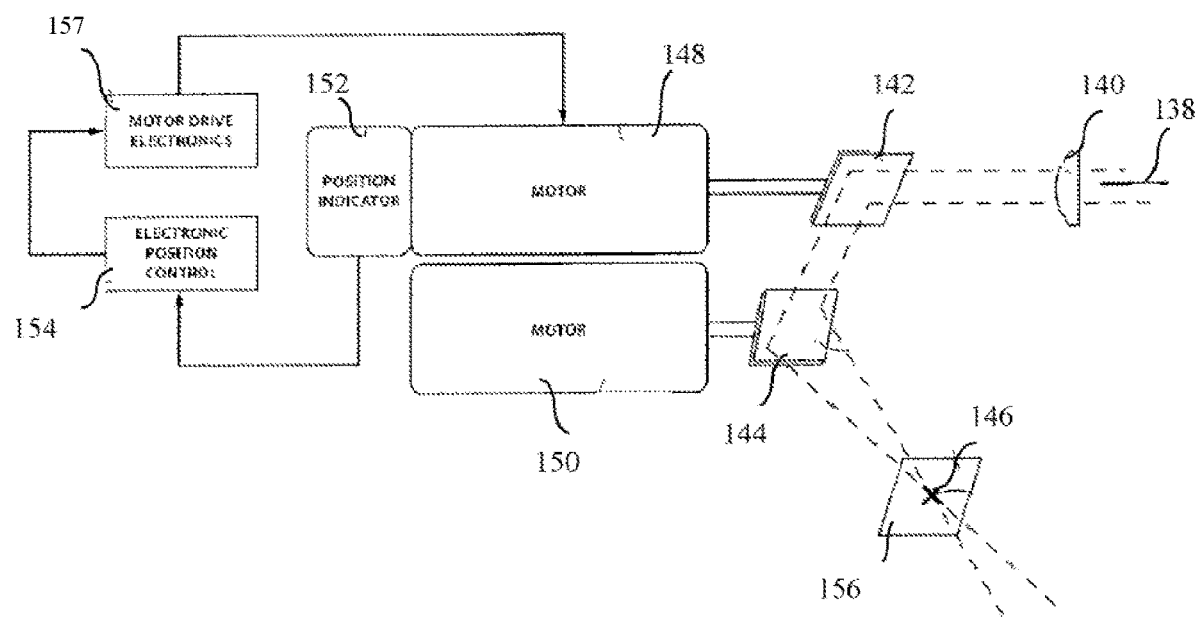
FIG. 5 is a schematic diagram showing a beam guidance system, according to various embodiments.

In various embodiments, the optical system for directing the laser beam to the treatment site can include mirrors controlled by galvanometers. An example schematic configuration is shown in FIG. 5. As shown, the treatment laser beam 138 can pass through a focusing lens 140 and the focused beam is directed by mirrors 142, 144. The mirrors 142, 144 can be moved in steps, such that the point of focus 146 of the treatment laser beam 138 can be moved along X and/or Y directions so as to cover substantially entirely a treatment area 156. In some embodiments, the mirrors 142, 144 are controlled by a positional closed loop feedback system that includes motors 148, 150. The motors 148, 150 typically include a galvanometer including an actuator for adjusting positions of the mirrors 142, 144. The positional loop associated with the motor 148 can include a sensor or position indicator 152, an electronic position control device 154, and motor drive electronics 157. A second positional control loop (not shown), which may utilize one or more of the components 152, 154, 157, can be associated with the other motor 150. As mentioned above, the optical system (e.g., shown in FIG. 5) can be located in the articulating arm 106, the main chamber 108, or any other suitable location.

Although FIG. 5 shows the treatment area 156 as having a generally square shape, this is for illustrative purposes only. In general, the motors 148, 150 can direct the laser beam 138 in a pattern (e.g., circular, raster, random, etc.) to form treatment areas having any shape, e.g., triangle, polygon, circle, oval, etc. In some embodiments, the shape of the treatment area 156 can be defined by the operator. The position control device 154 can be provided with information about the treatment area 156. Such information may include the size and shape of the treatment area 156. The position indicator 152 can determine the relative position of the point of focus 146 of the laser beam 138 within the treatment area 156 at a particular instance. Based on the relative position obtained from the position indicator 152, the position control device 154 can determine the movement of the motor 148 during the next step of operation. These steps can be determined for each of the motors 148, 150 such that the laser beam 138 is substantially confined to the treatment area 156, and covers (e.g., treats) the area 156 in a desirable manner. This positional closed-loop feedback system enables an operator to select and/or define a treatment area 156 and to automatically treat the entire selected and/or defined area, without substantially affecting adjacent tissue portions. In various embodiments, the motors 148, 150 can adjust the mirrors 142, 144 at a rate in a range from 2,500 steps per second to 500,000 steps per second. Additional parameters of the beam guidance system are shown in FIG. 6.

Figure 7:
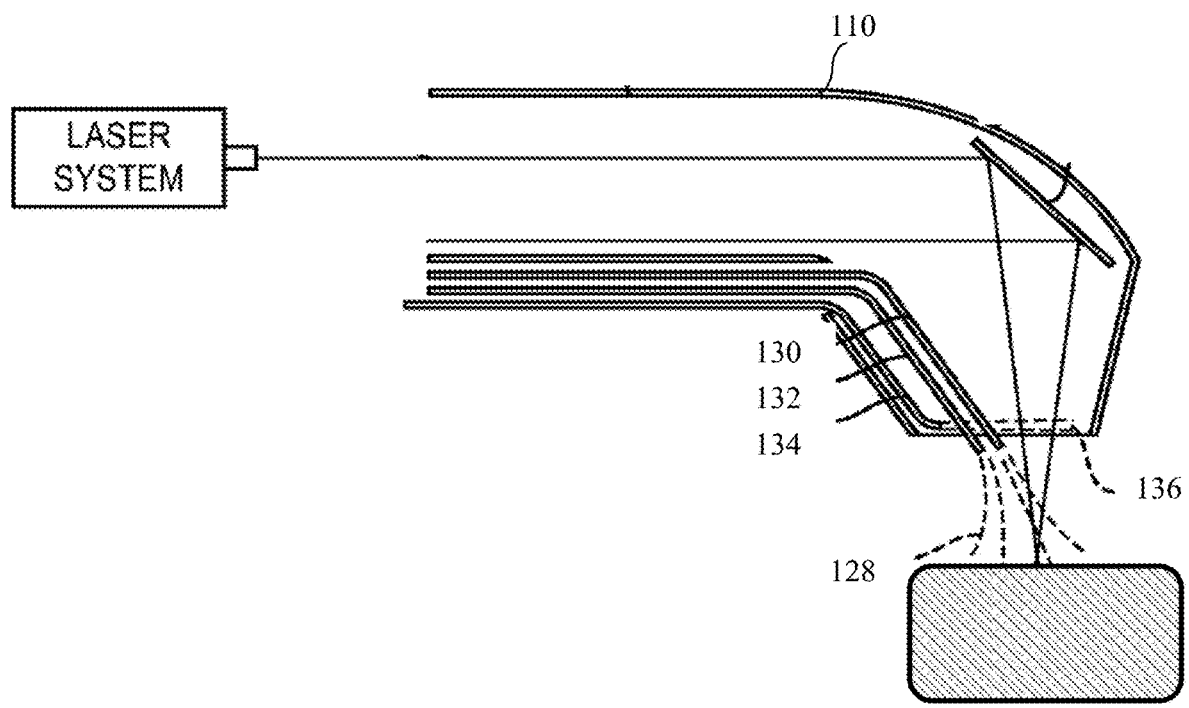
FIG. 7 is a schematic cross-sectional view of a hand piece including a cooling system, according to various embodiments.

In various embodiments, the system 100 can be adapted to control a temperature of a treatment region below a particular threshold. For example, as shown in FIG. 2, pressurized air and/or coolant can be directed to the treatment site. As shown in FIG. 7, cooling fluid 128 can be directed to the treatment site via nozzles 130 and 132. This fluid can provide both the cooling to control the cutting and also help to remove the cut material from the treatment site. In some instances, a separate nozzle assembly 134 can supply an air curtain 136 that may keep the cooling fluid from splashing back into the hand piece 110. The separate nozzle assembly 134 can supply a controlled amount of air such that the air curtain 136 substantially forms a laminar flow, which can minimize the disruption to the laser beam. The flow of the coolant fluid 128 is generally controlled such that the cuts can be achieved consistently and in a repeatable manner using the laser beam. In some cases, the coolant can also enable improved interaction/coupling between the laser beam and the treatment surface. The flow rate of the coolant can be controlled within a range of 10 $mm^3$/min to 1,000 $mm^3$/min and can be applied at a pressure in a range from 50 psi to 400 psi. Additional example cooling parameters are shown in FIG. 8.

In other embodiments, the system 100 does not include a cooling system for cooling the treatment site. For certain cutting applications, cooling may not be necessary, e.g., treatment of tissue regions with sensitivity and/or structural characteristics (e.g., moisture content) different than that of a tooth.

In various embodiments, the system 100 is adapted to configure the output laser beam with a particular polarization in order to improve cutting performance. Polarization, as used in this application, refers to the direction of the electric field component of the laser's electromagnetic wave oscillations. While a brief background on the concept of polarization is helpful, for brevity, the background will describe the concept of polarization with respect to light; however, the same concepts apply to laser electromagnetic radiation. When light is incident on a tissue, the light undergoes several mechanisms of reflection, refraction, absorption, and scattering. One way to determine the amount of light that propagates through a particular material is with reference to the index of refraction, which is a dimensionless value that relates to how much a path of light is bent (or refracted) when entering a material. A birefringent material is a material that has different refractive indexes depending on the polarization of the light impinging upon the material. Said another way, light having certain polarizations propagate into the material, while light having other polarizations can be reflected or scattered off the material. In some instances, this application will describe polarization with respect to either light or laser electromagnetic radiation; however, the concepts describes herein are applicable to both light and laser electromagnetic radiation, as would be understood by the person having ordinary skill in the art.

In general, hard tissues are birefringent materials that exhibit positive birefringence (i.e., allow light/lasers to propagate therethrough) along the orientation of their collagen fibers. Bones are one example of a hard tissue containing collagen fibers. Bones are composed primarily of collagen fibers as an organic component and an inorganic component (primarily hydroxyapatite). The orientation of collagen fibers (e.g., similar to an alternating wood grain laminated plywood-like structure), which are on the micro length scale in the form of a fibrillar network, has been shown to have an influence on bone mechanics, e.g., tensile strength and elastic modulus. One aspect of the invention disclosed herein includes using the orientation of the collagen fibers to enable improved treatment with polarized light/lasers.

Figure 9:
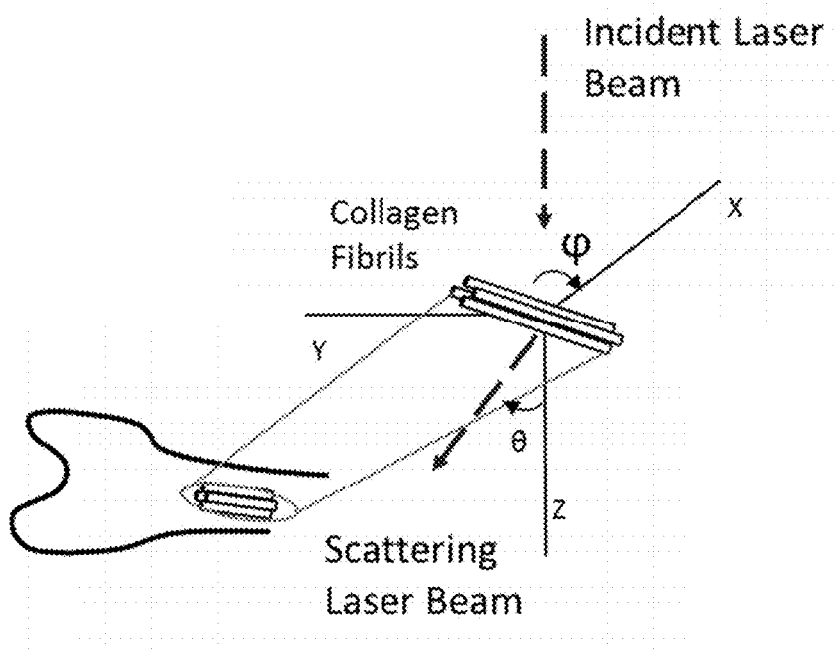
FIG. 9 is an diagram illustrating a laser beam incident upon collagen fibrils.

This concept is illustrated in FIG. 9, which depicts a laser beam that encounters a bone surface at some angle of incidence with respect to the bone's collagen fibers (or fibrils as labelled in the figure). Upon contacting the bone surface, the light scatters such that its trajectory is deflected by an angle $\theta$ in the scattering plane (which in some cases is the same or about the angle of incidence) and by an azimuthal angle $\phi$ (0 to $2\pi$) in the perpendicular plan. The portion of the laser beam having an electric field (polarization) parallel to the collagen fibrils is absorbed much more than the portion having an electric field (polarization) perpendicular to the collagen fibrils.

Thus, directing a laser beam polarized along the axis of orientation of the collagen fibers of the tissue (e.g., minimizing the perpendicular component of the laser beam shown in FIG. 9) can maximize the absorption of the laser energy by the tissue, resulting in superior and faster cutting performance. By minimizing the incidence angle between the scattering plane and that of the electric field of the laser, absorption of energy deposited onto the tissue can be optimized.

In view of the foregoing, in some embodiments the system 100 is adapted to control the orientation of the laser's electric field (i.e., the laser's polarization) to coincide with the orientation and the distribution of the collagen fibers. The system 100 can feature various alternative configurations to accomplish the polarization, a few examples of which are described below.

In various embodiments, linear and/or circular polarization of the laser beam is performed by introducing a birefringent material (e.g., made of quartz or mica) such as a half waveplate or a quarter waveplate or a combination of both into the main chamber 108 and/or the hand piece 110. As described above, linearly polarized light travels along a single linear axis and can be oriented in a desired direction (e.g., to align with the collagen fibers of bone). Circularly polarized light, on the other hand, includes equal amounts of s-polarization and p-polarization for any beam orientation. In general, p-polarization is a portion of the light having an electric field direction parallel to the plane of incidence and s-polarization is a portion of the light having an electric field direction perpendicular to the plane of incidence. Therefore, circularly polarized light impinges all axes of a treatment surface with the same composition of polarization, and material is removed uniformly regardless of cut direction and angle. In such instances, the portion of the circularly polarized light having a scattering angle of 0° can be particularly effective at cutting. In some instances, light is first linearly polarized and then phase shifted, such that it is circularly polarized.

Figure 10:
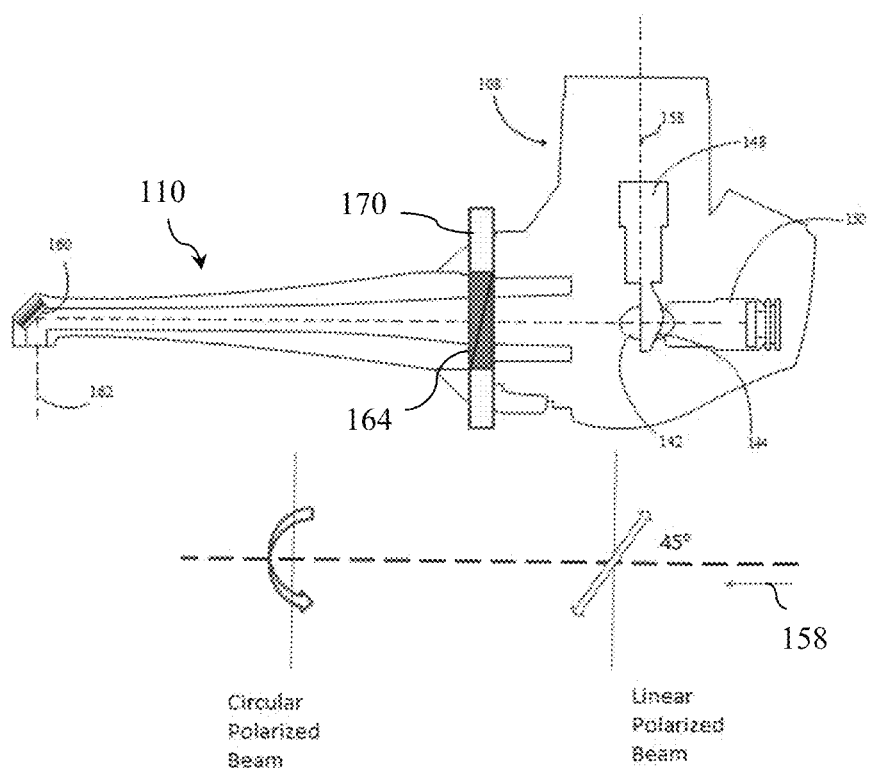
FIG. 10 is a schematic cross-sectional side view of a hand piece configured to generate a polarized treatment beam, according to various embodiments.

FIG. 10 depicts an example configuration of the main chamber 108/hand piece 110 that is adapted to deliver circularly polarized light to a treatment surface. As shown, a circular polarizer 164 can be mounted along the laser beam delivery axis 158 within the main chamber 108 and/or hand piece 110 such that the laser beam is circularly polarized when it passes through the quarter wave plate 164 and remains circularly polarized when it is reflected off of a turning mirror 160 and delivered to a treatment region. In general, any circular polarizer 164 can be used, for example, a quarter wave plate, a reflective phase retarder, etc. As shown in FIG. 10 in some embodiments, the beam incident upon the circular polarizer 164 can be linearly polarized. The linear polarization can take place at any location upstream of the circular polarizer, e.g., at the laser source 102, within the articulating arm 106 within the main chamber 108, etc. In some instances, the linearly polarized light is delivered directly to the treatment site without being circularly polarized.

Figure 11:
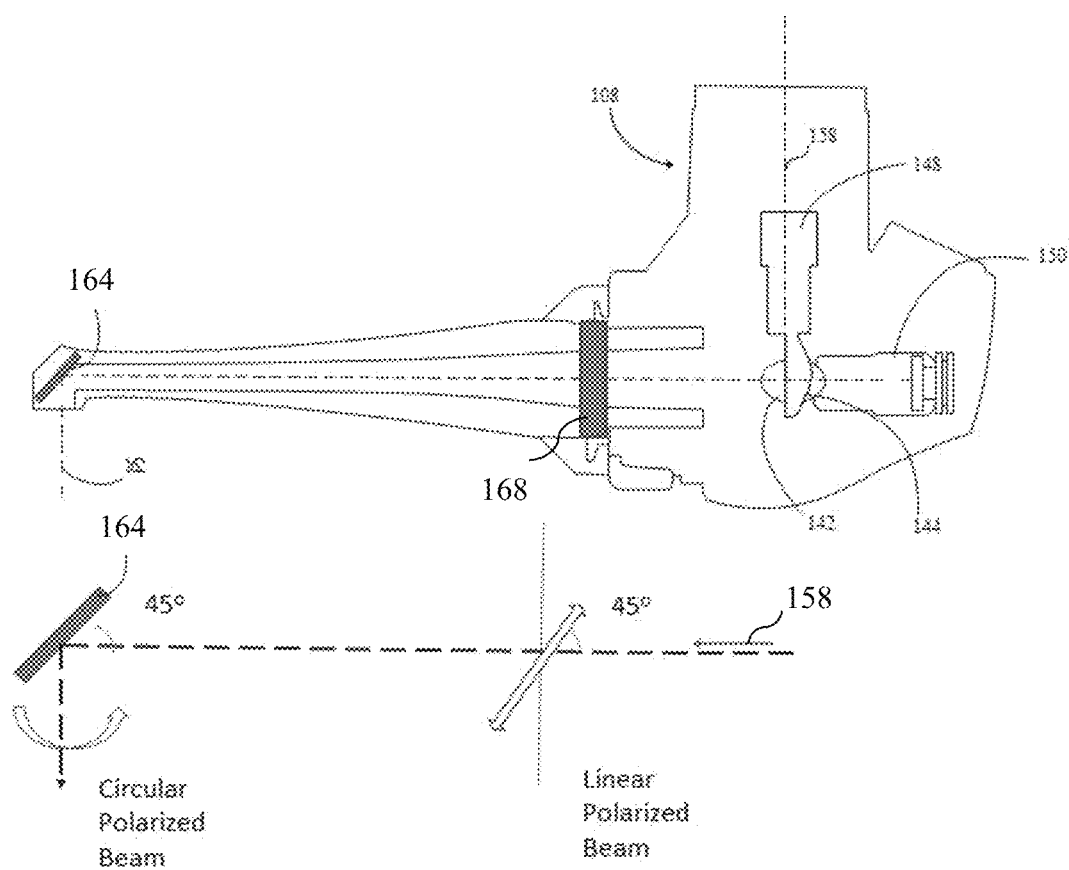
FIG. 11 is a schematic cross-sectional side view of a hand piece configured to generate a polarized treatment beam, according to different embodiments.

In another embodiment, shown for example in FIG. 11, the laser beam can be circularly polarized by replacing the turning mirror 160 with a circular polarizer 164 (e.g., arranged at a 45° angle). In such embodiments, the laser beam may also be passed through a linear polarizer 168, which can be mounted within the main chamber 108 and/or hand piece 110 upstream of the circular polarizer 166. In general, any linear polarizer can be used, e.g., a half wave plate. Converting linear polarization to circular polarization can eliminate cutting variations. In general, the circular polarizer 164 and/or the linear polarizer 168 can be mounted in any desirable location with the system 100, e.g., the laser source 102, articulating arm 106, main chamber 108, hand piece 110, etc. In some instances, the linear polarizer 168 can linearly polarize the beam such that the beam has a particular plane of polarization (e.g., 45° to the plane of incidence) and is incident on the circular polarizer 164 oriented along the same plane (e.g., 45° to the plane of incidence).

Figure 12:
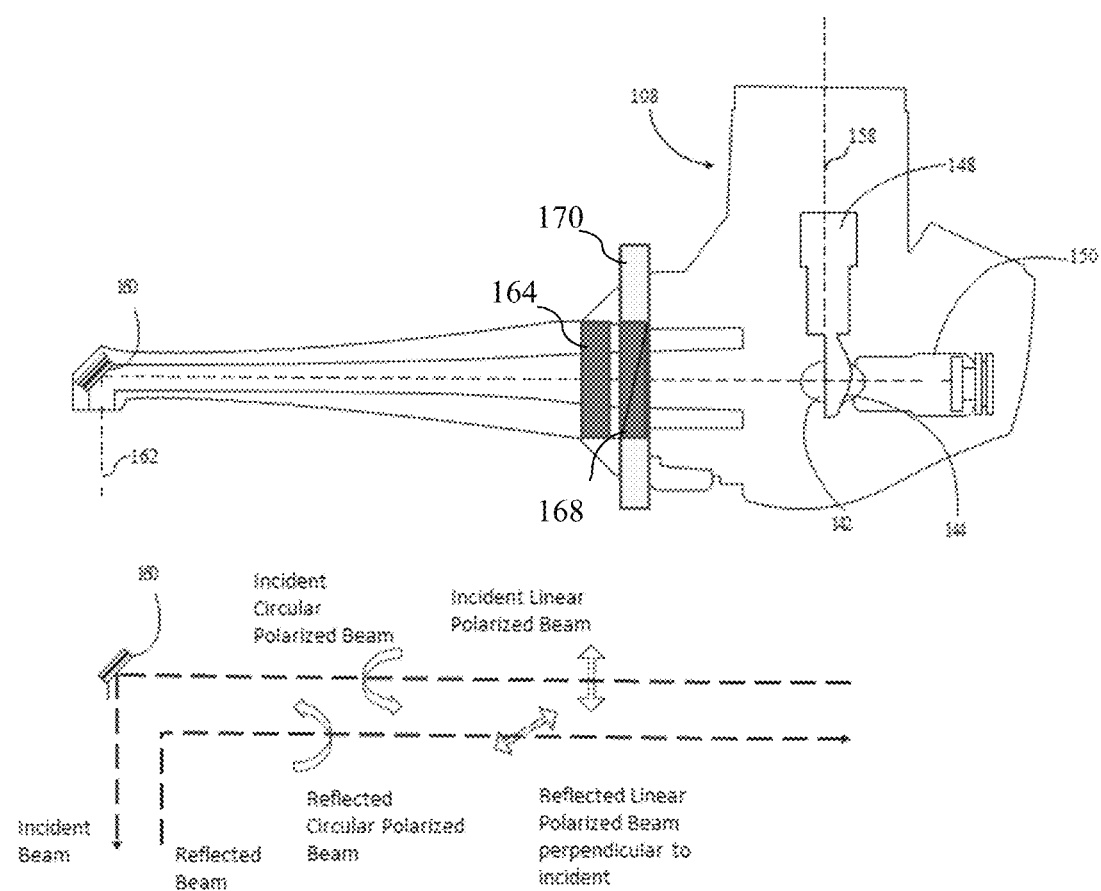
FIG. 12 is a schematic cross-sectional side view of a hand piece including a rotatable polarizer, according to various embodiments.

In various embodiments, a linear polarizer 168 (e.g., a half wave plate) and a circular polarizer 164 (e.g., a quarter wave plate) can be combined, as shown for example in FIG. 12. The linear polarizer 168 can generate a linearly polarized beam and the circular polarizer 164 (e.g., mounted downstream of the linear polarizer 168) can generate a circularly polarized beam that is directed onto the treatment region. In some instances, the linear polarizer 168 and/or circular polarizer 164 can be adapted to block light that is reflected from the treatment site. For example, in some cases the system can include another polarizer (e.g., different than linear polarizer 168) that blocks any reflected light that passes through the linear polarizer 168. In some instances, the other polarizer is a linear polarizer with an opposite orientation to the linear polarizer 168. Thus, in such instances, all or substantially all reflected light is blocked.

In various embodiments, the system 100 can determine the orientation of the tissue collagen (or other relevant structure) using an imaging system as described with reference to FIGS. 13 and 14 below. Once the orientation is known, the linear and/or circular polarization can be adjusted with respect to the orientation of the collagen (e.g., to better align with the collagen) and improve cutting performance.

In various embodiments, the system 100 can be adapted to manipulate the power levels of the output laser beam by controlling the polarization of the beam. In general, any technique for controlling polarization can be used. For example, the circular polarizer 164 and/or linear polarizer 168 can be mounted on a rotational mount 170 (see FIG. 10 and FIG. 12) to enable rotation of the circular polarizer 164 and/or linear polarizer 168. In general, any type of rotational mount 170 can be used, e.g., a bar mount, a ring mount, a kinematic mount, a gimbal mount, etc. Rotation of the polarizers can change the power output of the beam, which can increase and/or decrease treatment performance (e.g., cutting speed). In general, the power output can be varied from 0 W to the maximum power output of the system 100 (e.g., 10,000 W).

In another aspect, the system 100 can be adapted to image the treatment area. For example, the system 100 can enable bones, nerves, and/or other body structures to be visualized and readily differentiated during a surgical procedure. Visualization of nerves during a procedure can allow the surgeon to avoid/minimize disrupting the nerves, which can result in fewer negative effects for the patient, such as reduced function, loss of sensation, and/or chronic pain. Similar concepts are applicable to the visualization of other anatomical structures, e.g., muscles, tendons, cartilage, blood vessels, etc.

Figure 13:
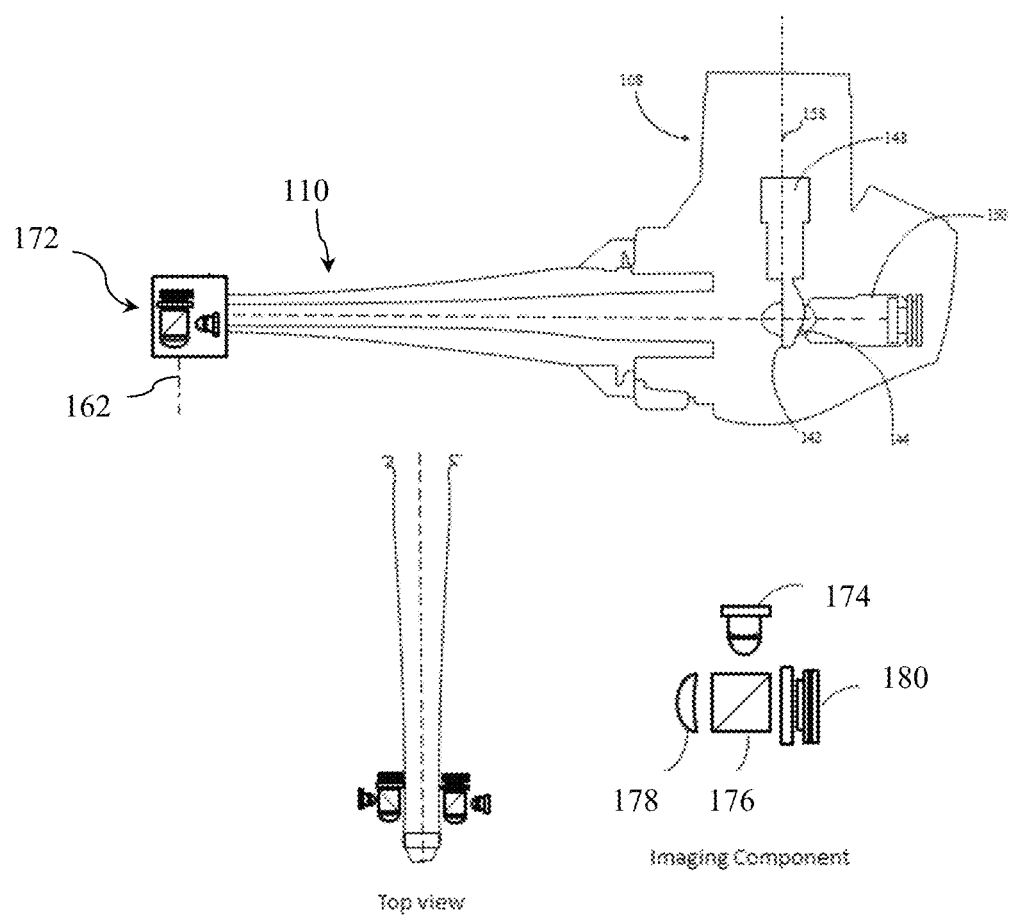
FIG. 13 is a schematic cross-sectional side view of a hand piece including an imaging system, according to various embodiments.
Figure 14:
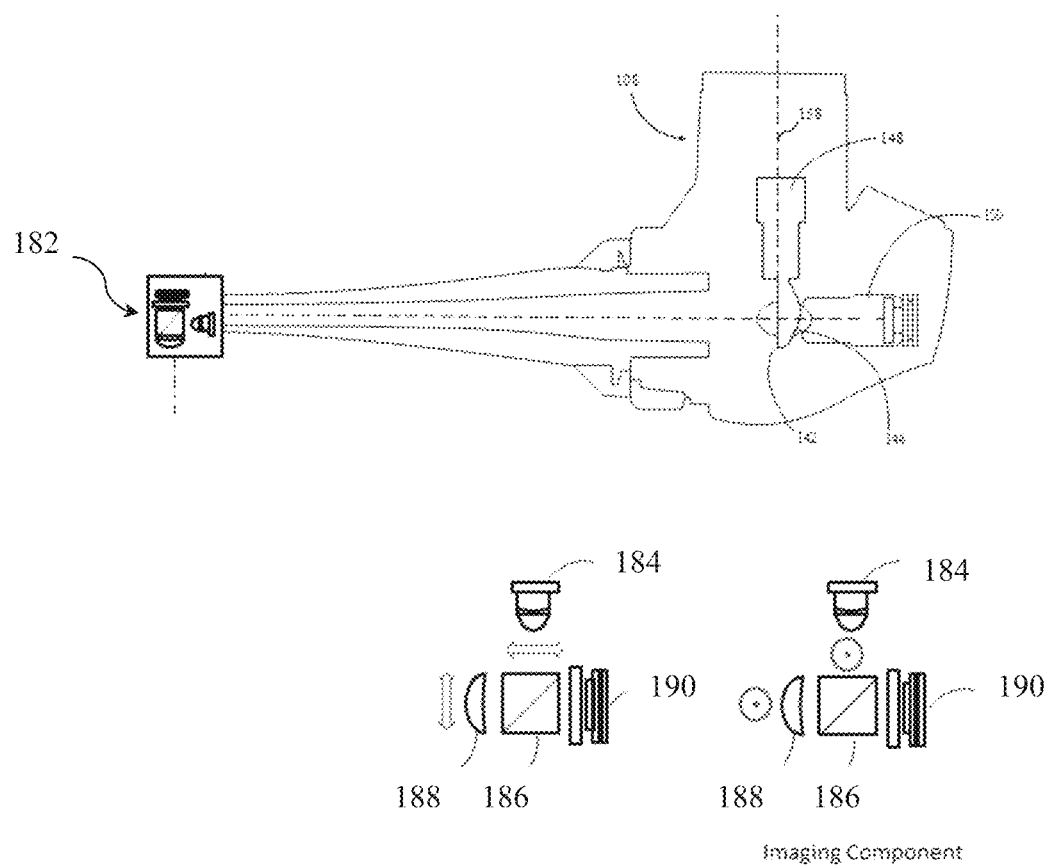
FIG. 14 is a schematic cross-sectional side view of a hand piece including a polarized imaging system, according to various embodiments.

In various embodiments, as shown for example in FIG. 13, the system 100 can include an imaging system 172. In general, any suitable imaging system 172 can be used. As one non-limiting example, the imaging system can include a light source 174, a beam splitter/filter 176 (e.g., for directing light emitted from the light source 174 to the treatment region), a lens 178, and a sensor 180 for receiving light rays reflected from the treatment region. As shown in the top view portion of FIG. 13, in some embodiments the imaging system 172 can be mounted to the exterior of the hand piece 110. However, in general, the imaging system 172 can be mounted/located in any desirable location, e.g., within the hand piece 110, main chamber 108, or articulating arm 106. In some embodiments, the imaging system can be a standalone system not mounted to the treatment system 100 at all. As also shown in the top view portion of FIG. 13, in some embodiments, the imaging system 172 can include two imagers (e.g., light source 174, beam splitter/filter 176, lens 178, and sensor 180). The two imagers can be arranged substantially symmetric about the cutting axis 162, which can enable 3D imaging of the treatment surface. In some such instances, the imaging components can be mounted at an angle in a range from 5 degrees to 30 degrees pointed at the center of the laser beam to provide a complete 360 degree field of view. In some instances, the sensor 180 can be coupled to a data acquisition board, which can be used for stereotype 3D rendering.

Figure 15:
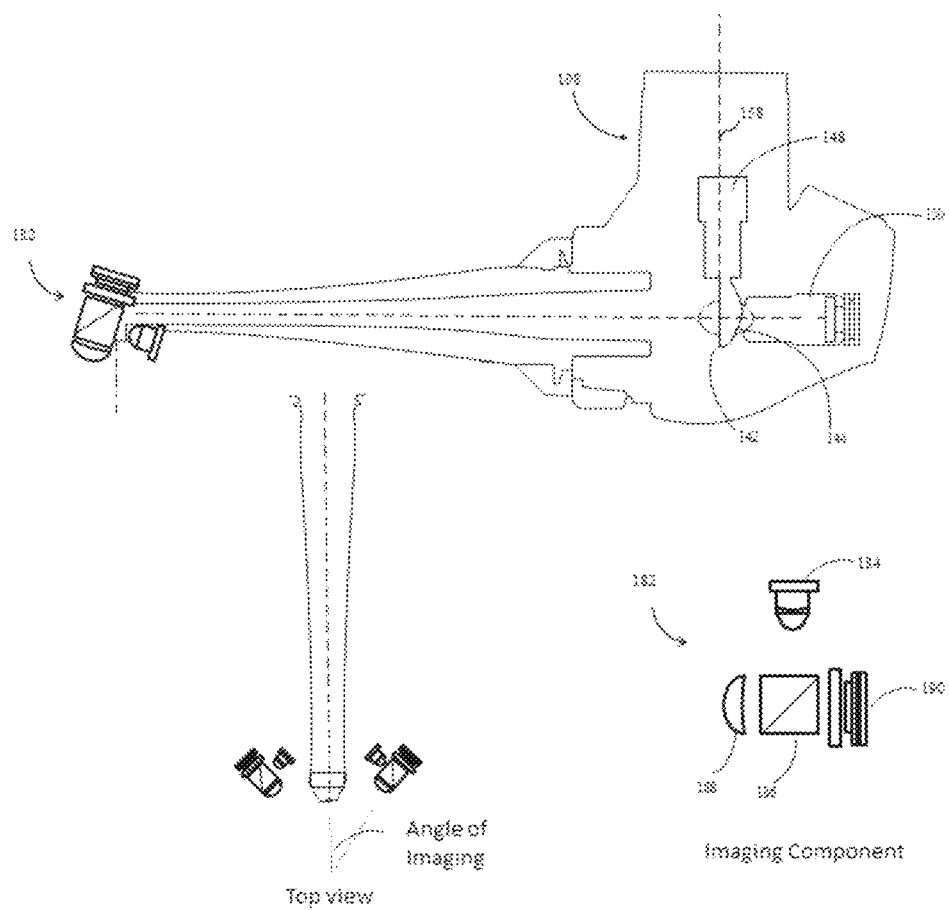
FIG. 15 is a schematic cross-sectional side view of a hand piece including a polarized imaging system arranged at an angle with respect to the laser beam, according to various embodiments.

In various embodiments, the imaging system can produce polarized light, which can enable improved visualization of anatomical structures comprised of birefringent materials (e.g., bones, nerves, etc.). For example, a polarized light imaging system 182 (FIG. 14) can provide the surgeon with improved contrast to visualize the collagen fibers and nerves which can improve the outcome of the procedure. The polarized light imaging system 182 can include a polarized illumination source 184, a linear polarizer 186 (e.g., a half wave plate), a focusing lens 188, and a sensor 190 (e.g., a CMOS/CCD sensor). In some cases, the linear polarizer 186 can direct the polarized light to the treatment surface, but other structures can also be used. As shown for example in FIG. 15, in some instances the polarized light imaging system 182 can be arranged at an angle (e.g., in a range from 0-45 degrees) with respect to the laser beam.

In some embodiments, the linear polarizer 186 can be rotationally mounted (e.g., using a bar mount, a ring mount, a kinematic mount, a gimbal mount, etc.). Rotating the linear polarizer 186 can alter the contrast of the received image. For example, the contrast of the collagen and/or nerves can increase or decrease as the linear polarizer 186 is rotated. When this light passes through a nerve, the tissue's unique internal structure can reflect the light in a way that is dependent on how the nerve fiber is oriented compared to the orientation of the polarization of the light. In general, the linear polarizer 186 can rotate any suitable amount (e.g., in a range up to ±90 degrees or ±180 degrees). In some embodiments, the linear polarizer can also be adapted to translate linearly along one or both axes any suitable amount (e.g., the entire linear dimension of the linear polarizer 186).

In some embodiments, two polarized light imaging systems 182 can be used (similar to the use of two imaging systems 172 shown in FIG. 13). In such embodiments, the linear polarizers 186 of each imager can be configured to detect orthogonally opposed states of polarization, which can enable rendering of a 3D image, e.g., by superimposing the two received images. Such data processing can be performed by the data acquisition board or any suitable processing device.

Figure 16A:
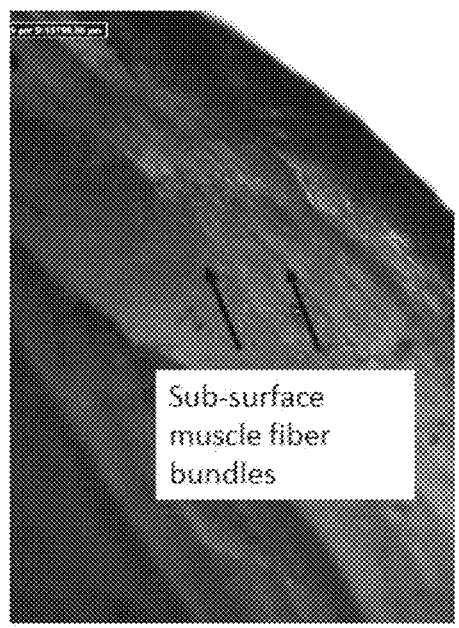
FIGS. 16A-B are example images of soft tissue imaged with and without a polarization imaging system.
Figure 16B:
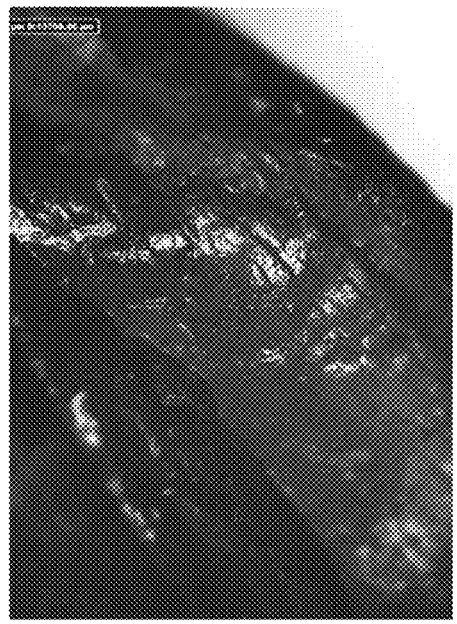
Figure 17A:
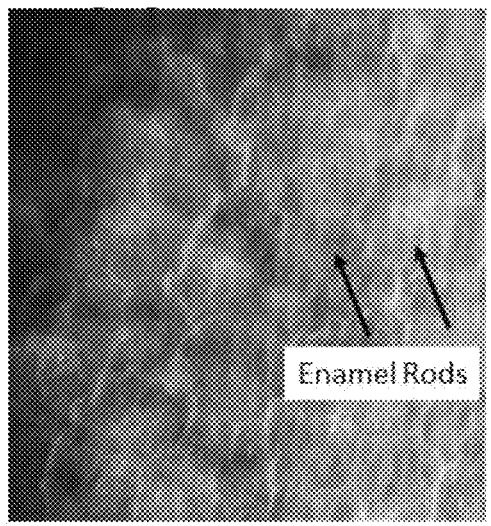
FIGS. 17A-B are example images of hard tissue imaged with and without a polarization imaging system.
Figure 17B:
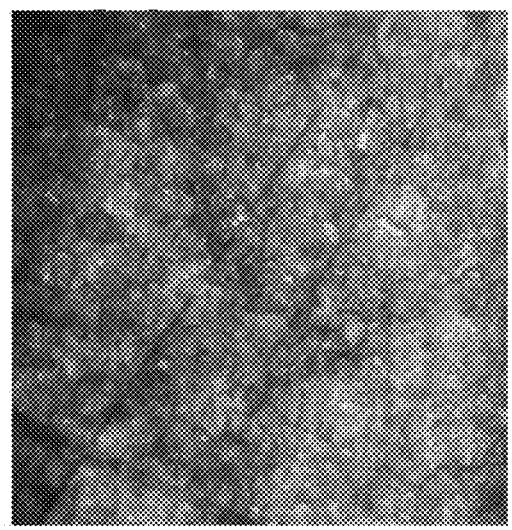

In various instances, the images collected by the imaging systems 172, 182 can be presented to the surgeon in any desirable format. In some instances the image can be displayed on the monitor 114 of the treatment system 100, or an external monitor. In some instances, the image can be displayed as a virtual reality or augmented reality overlay (e.g., using a virtual reality of augmented reality headset or other device worn by the surgeon). FIG. 16A is an example image of soft tissue taken with a polarized imaging system (with sub-surface muscle fiber bundles identified) and FIG. 16B is an example image of soft tissue taken with a conventional (non-polarized) imaging system. FIG. 17A is an example image of hard tissue taken with a polarized imaging system (with enamel rods identified) and FIG. 17B is an example image of hard tissue taken with a conventional (non-polarized) imaging system Each numerical value presented herein is contemplated to represent a minimum value or a maximum value in a range for a corresponding parameter. Accordingly, when added to the claims, the numerical value provides express support for claiming the range, which may lie above or below the numerical value, in accordance with the teachings herein. Every value between the minimum value and the maximum value within each numerical range presented herein (including in the charts shown in the figures), is contemplated and expressly supported herein, subject to the number of significant digits expressed in each particular range. Absent express inclusion in the claims, each numerical value presented herein is not to be considered limiting in any regard.

Unless expressly described elsewhere in this application, as used herein, when the term "substantially" or "about" is before a quantitative value, the present disclosure also includes the specific quantitative value itself, as well as, in various cases, a ±1%, ±2%, ±5%, and/or ±10% variation from the nominal value unless otherwise indicated or inferred.

Having described herein illustrative embodiments, persons of ordinary skill in the art will appreciate various other features and advantages of the invention apart from those specifically described above. It should therefore be understood that the foregoing is only illustrative of the principles of the invention, and that various modifications and additions, as well as all combinations and permutations of the various elements and components recited herein, can be made by those skilled in the art without departing from the spirit and scope of the invention. Accordingly, the appended claims shall not be limited by the particular features that have been shown and described, but shall be construed also to cover any obvious modifications and equivalents thereof.

What is claimed is:

1. A laser-based treatment system for treating a tissue, the system comprising:
   a laser source for generating a laser beam;
   a hand piece optically connected to the laser source and comprising (i) an optical component for directing the laser beam at a treatment surface of the tissue and (ii) an imaging system for imaging the treatment surface;
   a controller for controlling at least one parameter of the laser-based treatment system such that the laser beam removes the tissue at a rate in a range from 1 gram per second to 3 grams per second; and
   at least one of a linear polarizer and a circular polarizer adapted to polarize the laser beam.

2. The system of claim 1, wherein the laser beam comprises a wavelength in a range from 9 μm to 11 μm.

3. The system of claim 1, wherein the laser-based treatment system is adapted to ablate the tissue.

4. The system of claim 1, wherein the laser-based treatment system is adapted to assist with insertion of a bone prosthesis.

5. The system of claim 4, wherein the imaging system is adapted to provide guidance and visualization of alignment for insertion of the bone prosthesis.

6. The system of claim 5, wherein the laser beam comprises a wavelength in range from 400 nm to 1 μm.

7. The system of claim 6, wherein the laser beam comprises at least one of a single wavelength and a broadband of multiple wavelengths.

8. The system of claim 1, wherein the tissue comprises a hard tissue.

9. The system of claim 8, wherein the tissue further comprises a soft tissue.

10. The system of claim 9, wherein the tissue comprises at least one of bone, muscle, tendon, cartilage, skin, and/or connective tissue.

11. The system of claim 10, wherein the laser-based treatment system is adapted to excise at least one of cartilage and bone in a procedure selected from the group consisting of a joint preparation, a femur osteotomy, and a humerus osteotomy.

12. The system of claim 10, wherein the laser-based treatment system is adapted to at least of prepare and expose joint cartilage.

13. The system of claim 1, wherein the laser source comprises a $CO_2$ laser source.

14. The system of claim 1, wherein the laser source comprises at least one of a He—Ne laser source, an argon laser source, a UV laser source, a Er-YAG laser source, and an excimer laser source.

15. The system of claim 1, wherein the laser beam comprises a pulse length in a range from 5 μs to 1,000 μs.

16. The system of claim 1, wherein the laser beam comprises a pulse energy in a range from 10 mJ to 100,000 mJ.

17. The system of claim 1, wherein the laser beam comprises a pulse repetition rate of 0.1 kHz to 4 kHz.

18. The system of claim 1, wherein the optical component comprises at least one of a galvanometer and a turning mirror.

19. A method of treating a tissue using a laser-based treatment system, the method comprising the steps of:
generating a laser beam having a wavelength in a range from 9 µm to 11 µm;
optically connecting the laser source to a hand piece, the hand piece comprising (i) an optical component for directing the laser beam at a treatment surface of the tissue and (ii) an imaging system for imaging the treatment surface;
controlling at least one parameter of the laser-based treatment system such that the laser beam removes the tissue at a rate in a range from 1 gram per second to 3 grams per second; and
polarizing the laser beam using at least one of a linear polarizer and a circular polarizer.

* * * * *